(12) United States Patent
Nelson et al.

(10) Patent No.: US 6,693,291 B2
(45) Date of Patent: Feb. 17, 2004

(54) DEVICE AND SYSTEM FOR IMPROVED IMAGING IN NUCLEAR MEDICINE AND MAMMOGRAPHY

(76) Inventors: Robert Sigurd Nelson, 2922 Upshur St., San Diego, CA (US) 92106; William Bert Nelson, 75 Mound Ave., Excelsior, MN (US) 55331-8570

( * ) Notice: Subject to any disclaimer, the term of this patent is extended or adjusted under 35 U.S.C. 154(b) by 0 days.

(21) Appl. No.: 10/461,242

(22) Filed: Jun. 13, 2003

(65) Prior Publication Data

US 2003/0209672 A1 Nov. 13, 2003

Related U.S. Application Data

(62) Division of application No. 09/590,089, filed on Jun. 7, 2000, now Pat. No. 6,583,420.

(51) Int. Cl.[7] .................. H01L 25/00; H01L 27/00; G01T 1/69; G01T 1/24
(52) U.S. Cl. ............... 250/505.1; 250/370.09; 250/397; 250/363.05; 250/363.01; 250/363.07; 250/363.08; 250/363.09; 250/370.08; 250/370.1; 359/641; 378/145; 378/151; 378/147; 378/148; 378/149
(58) Field of Search .................. 250/505.1, 370.09, 250/370.08, 370.1, 397, 363.05, 363.01, 363.07, 363.08, 363.09; 359/671; 378/145, 151, 147, 148, 149

(56) References Cited

U.S. PATENT DOCUMENTS 5,939,724 A * 8/1999 Eisen et al. ............ 250/370.09
6,583,420 B1 * 6/2003 Nelson et al. ............... 250/397
2003/0205675 A1 * 11/2003 Nelson et al. ......... 250/370.09
2003/0205676 A1 * 11/2003 Nelson et al. ......... 250/370.09
2003/0209662 A1 * 11/2003 Nelson et al. ........... 250/252.1
2003/0209672 A1 * 11/2003 Nelson et al. .............. 250/394

* cited by examiner

Primary Examiner—John R. Lee
Assistant Examiner—Bernard Souw

(57) ABSTRACT

A method and apparatus for detecting radiation including x-ray, gamma ray, and particle radiation for radiographic imaging, and nuclear medicine and x-ray mammography in particular, and material composition analysis are described. A detection system employs fixed or configurable arrays of one or more detector modules comprising detector arrays which may be electronically manipulated through a computer system. The detection system, by providing the ability for electronic manipulation, permits adaptive imaging. Detector array configurations include familiar geometries, including slit, slot, plane, open box, and ring configurations, and customized configurations, including wearable detector arrays, that are customized to the shape of the patient. Conventional, such as attenuating, rigid geometry, and unconventional collimators, such as x-ray optic, configurable, Compton scatter modules, can be selectively employed with detector modules and radiation sources. The components of the imaging chain can be calibrated or corrected using processes of the invention. X-ray mammography and scintimammography are enhanced by utilizing sectional compression and related imaging techniques.

7 Claims, 24 Drawing Sheets

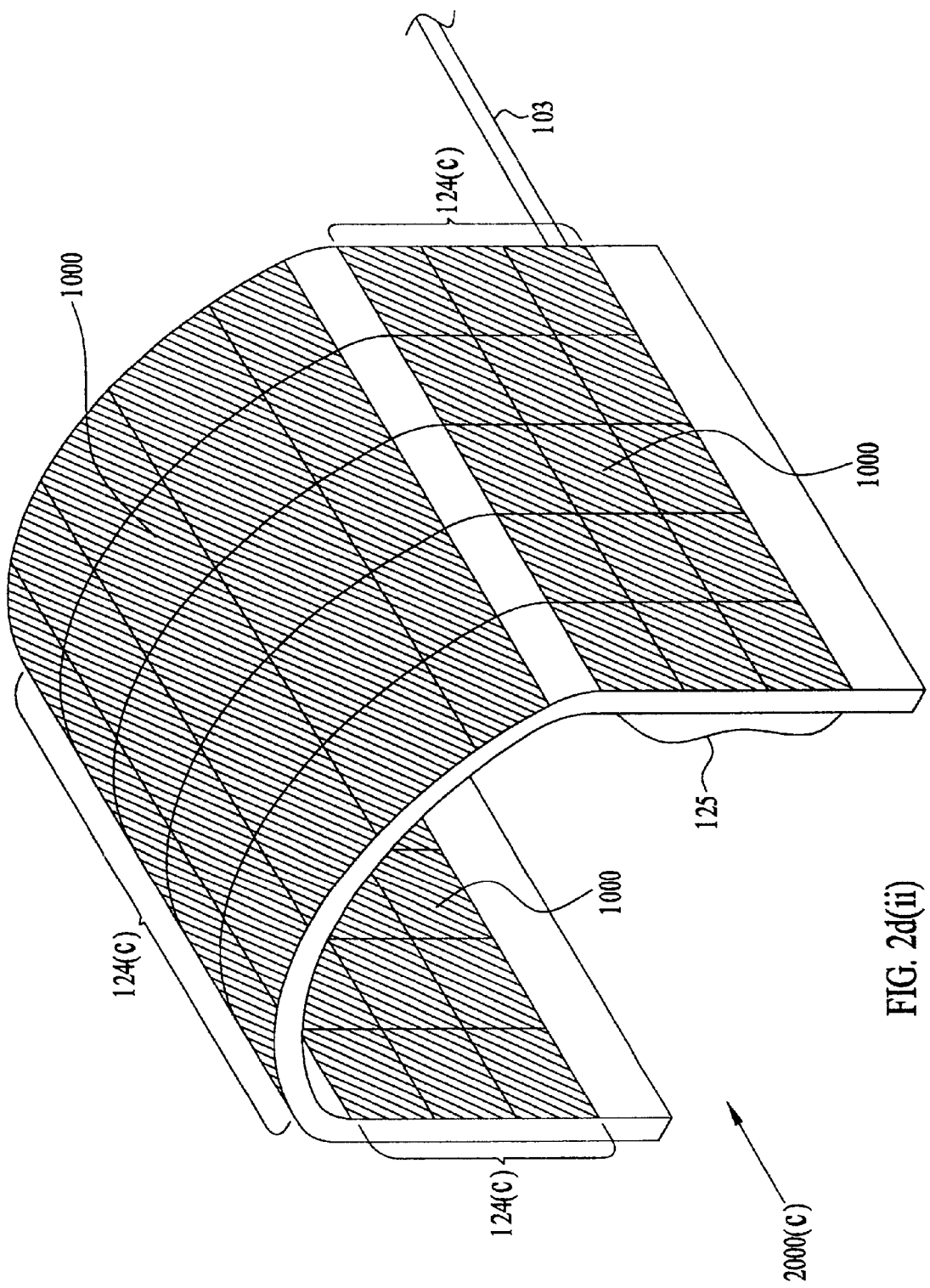
FIG. 2d(ii)

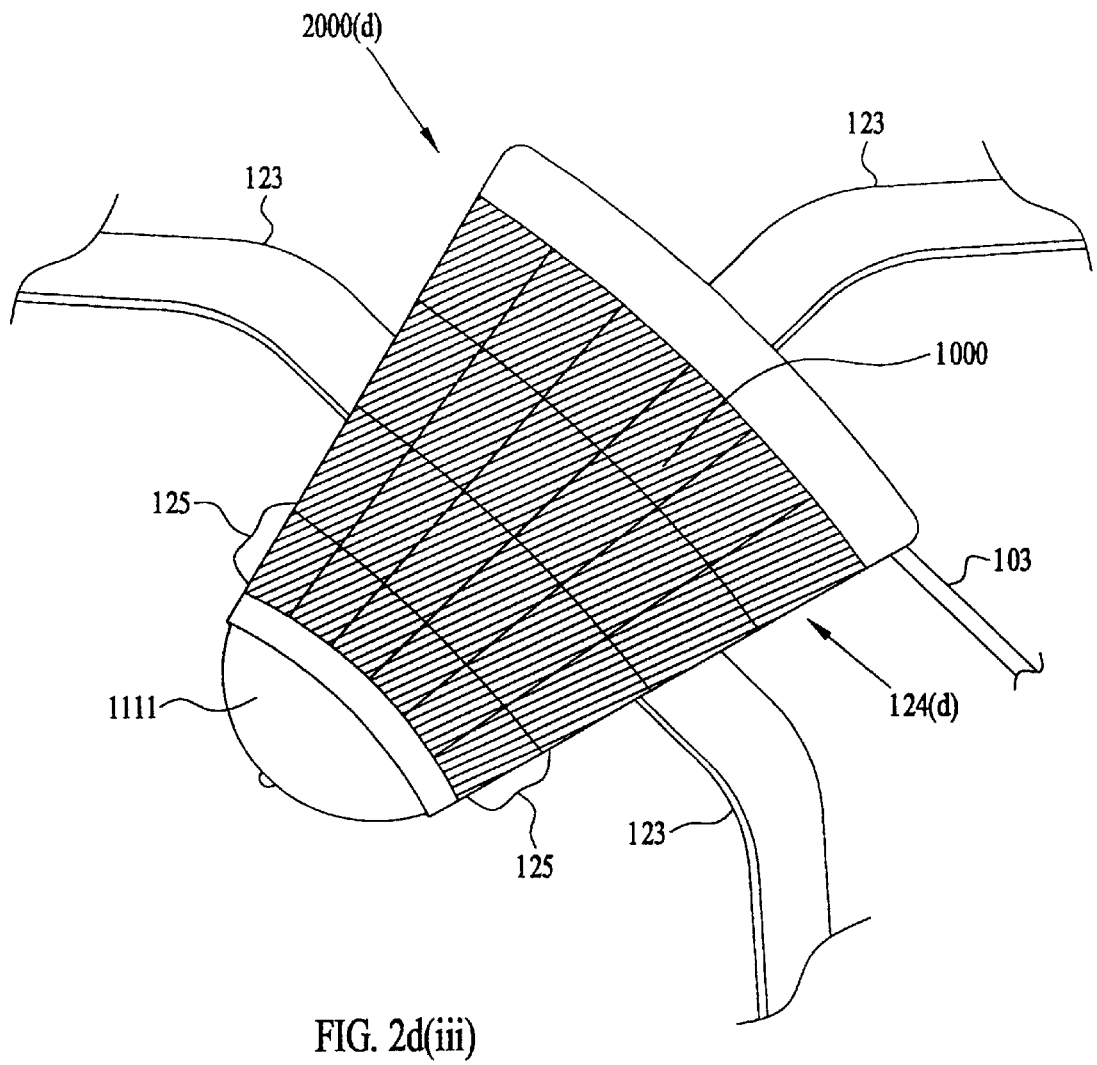
FIG. 2d(iii)

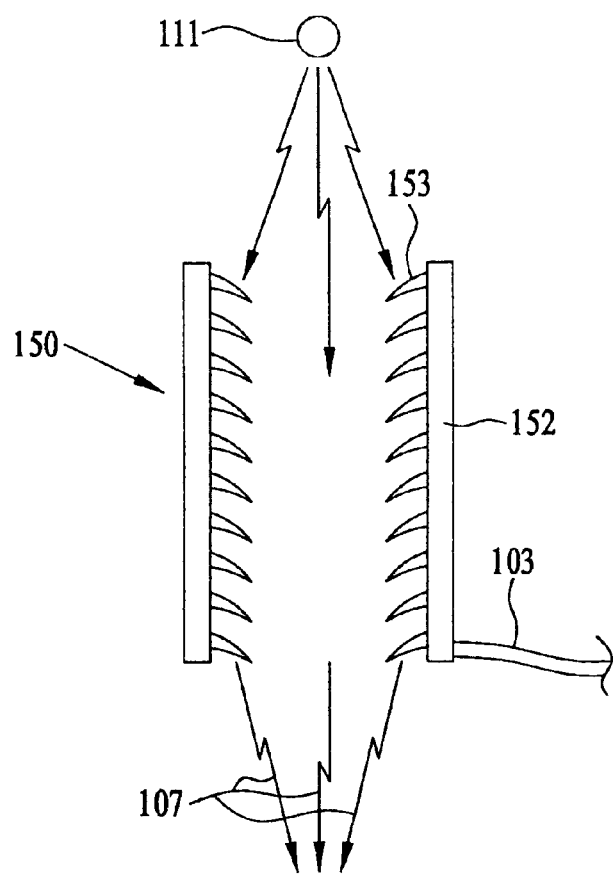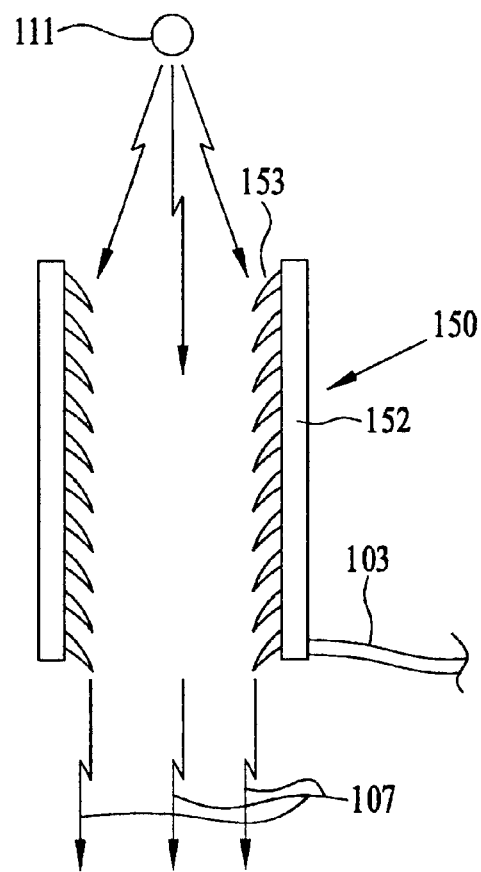
FIG. 5a(i)        FIG. 5a(ii)

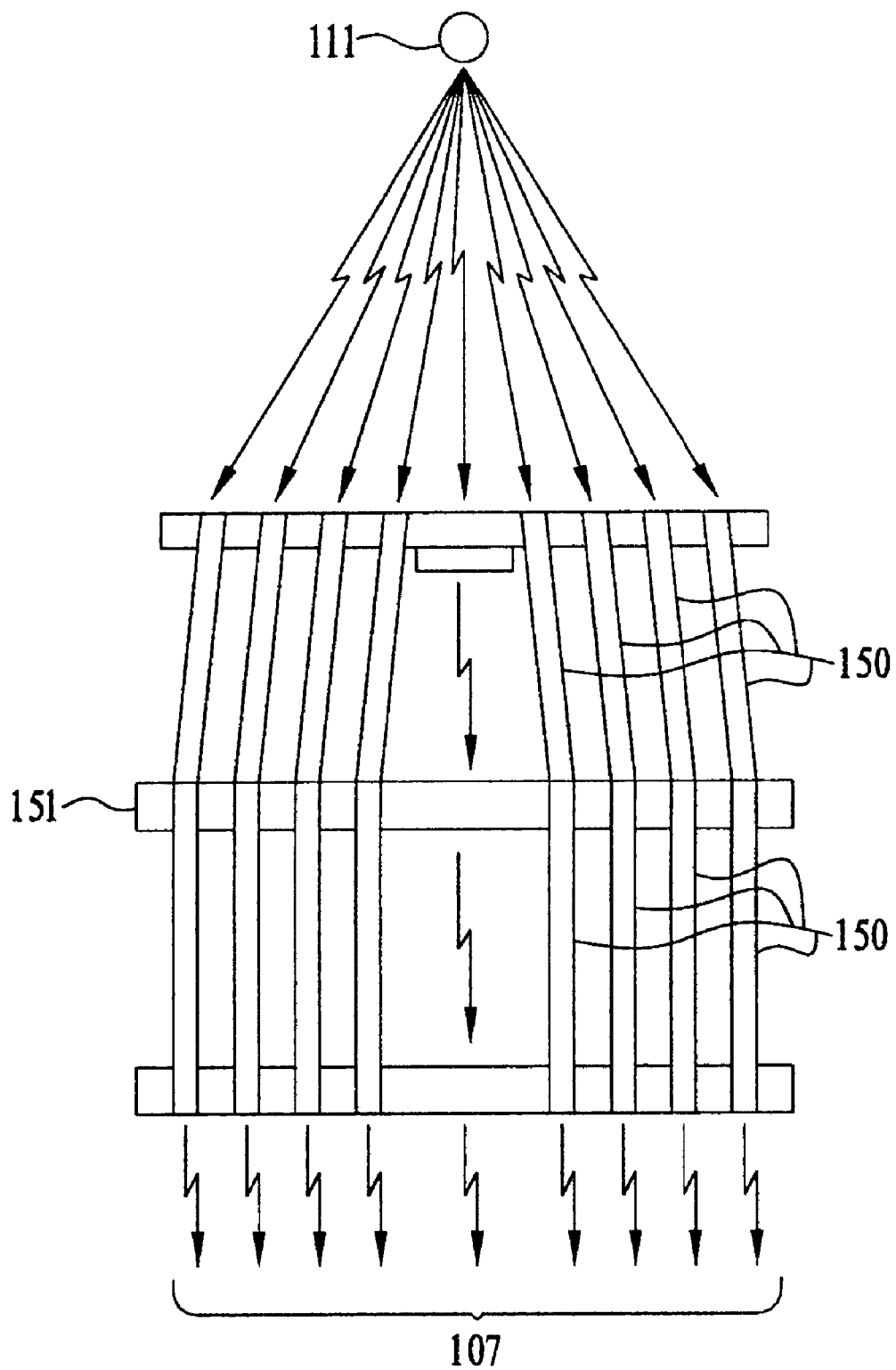
FIG. 5b (ii)

DEVICE AND SYSTEM FOR IMPROVED IMAGING IN NUCLEAR MEDICINE AND MAMMOGRAPHY

This application Ser. No. 10/461,242 is a divisional application of the U.S. application Ser. No. 09/590,089 filed Jun. 7, 2000, now U.S. Pat. No. 6,583,420.

FIELD OF THE INVENTION

This invention relates to an improved system for radiographic imaging and material analysis and more specifically for nuclear medicine and mammography imaging.

BACKGROUND OF THE INVENTION

Two general imaging problems in radiology involve the determination of a radiation source distribution and/or the effect of a filter, in this case a patient, on the radiation source distribution. Consider the field of nuclear medicine where the radiation source or other radionuclide distribution emits photons or positrons. Image data acquisition in nuclear medicine presents several challenges in addition to constraints imposed by finite acquisition times and patient exposure restrictions. Most photon energies that are of interest in nuclear medicine are higher than the typical photon energies employed in diagnostic x-ray radiography. In particular, Positron Emission Tomography (PET) involves the detection of pairs of very high energy photons due to annihilation events. Unfortunately, the photon radiation source, such as a radionuclide, used in nuclear medicine is not directional and the source distribution within the body is not precisely known.

Photons that escape the body may be scattered, altering their energies and/or direction vectors. It is desirable for many applications to discriminate against scatter radiation reaching the detector based on energy and/or direction. It may also be desirable to only detect radiation with a specific direction vector, since many detection systems possess poor directional discrimination capability and have finite response times within which to detect events, thereby limiting detection rates. Thus detection systems used in nuclear medicine such as Gamma cameras or PET scanners often employ conventional, such as attenuating or rigid geometry, focused or unfocused collimators, often referred to as grids or grid collimators, to help define the direction vectors of a detected photons. The direction vectors and energies of non-scattered photons are well-defined. Unfortunately, the emission of photons from the source distribution is non-directional and the radiation source distribution itself is typically not well-defined. A Compton-scattered photon suffers an energy loss and change in direction vector whereas a coherent or Rayleigh scattered photon only has its direction vector altered. In general x-ray radiography the source is a x-ray tube, although a radionuclide maybe substituted, used in a point, slit, slot, or area imaging configuration. The energy distribution and direction vector of the radiation from a x-ray tube are approximately known. These parameters are typically well-defined for a collimated radionuclide source used in an application such as point-scan Compton scatter imaging and material analysis. A number of detection formats are in use depending on the application. A planar detector geometry is typically utilized for applications such as mammography, angiography, and chest radiography which typically employ detectors such as x-ray film-screen devices, or storage phosphor screens, or image intensifiers coupled to cameras. Slit- and slot-scan formats are also available, usually incorporating improvements to the detectors and, in some instances, the radiation source. Additional image acquisition formats include ring-shaped detectors or flat detectors for fan-beam or cone-beam tomography, respectively. Common detector geometries used in nuclear medicine typically include one or more planar detectors, which are basically standard Gamma cameras, with attached conventional collimators or ring detectors, used in Positron Emission Tomography. Imaging systems based on standard Gamma camera and related detector designs are frequently used for a number of nuclear medicine studies such as heart, brain, thyroid, gastro-intestinal, whole body, and breast imaging, including scintimammography. A basic Gamma camera design employs a large, planar array of scintillation crystals or a single, large, planar scintillation crystal optically coupled to an array of photomultiplier tubes (PMTs). A conventional focused or unfocused collimator is typically mounted to the face of the Gamma camera. This inflexible imaging system is then positioned such that the region of interest containing the source distribution is within the field of view. It provides a limited degree of spatial resolution and energy resolution while removing some fraction of unscattered and scattered radiation that would otherwise degrade image quality. Unfortunately a substantial fraction of useful unscattered radiation is also attenuated. Another infrequently used design replaces the conventional collimator with a coded aperture such as a uniformly redundant array aperture which is also based on photon attenuation and is typically rigid. Commercial systems may use one, two, or three Gamma camera detector units. One commercial system eliminates the use of scintillator crystals and PMTs with a rigid, planar, 2-D CdZnTe semiconductor detector manufactured by abutting four 2-D CdZnTe arrays of moderate size. Techniques for abutting 2-D silicon arrays are well-known in the art. Drawbacks to employing large- or medium-sized 2-D CdZeTe arrays capable of high detection efficiency include the difficulty of growing thick CdZnTe crystals with acceptable levels of defects and creating a low noise, 2-D array readout structure on top of a large- or medium-size CdZnTe crystal. Grid collimators are still desirable for many applications since the direction vectors of detected photons are otherwise poorly defined. A design which replaces a conventional collimator with a relatively thin, planar semiconductor, often Ge, array of moderate size, which serves as a Compton scatterer is referred to as a Compton electronic Gamma camera. This system is still being refined. The detector module array described below can be used in place of a standard Gamma camera in a Compton Gamma camera system.

Nuclear medicine imaging applications are complicated by the fact that the spatial distribution of the source within a region of the patient is poorly defined. One way to simplify this problem is to use emitted photons of known energies. For example, a source that has one or more emission energies of a narrow energy bandwidth may be utilized. The problem now is the reconstruction of the source distribution rather than the calibration of the source distribution. The measured source distribution, i.e., the apparent source distribution, represents the filtered true source distribution, assuming self-attenuation is small. In certain nuclear medicine applications estimates of the true source distribution are obtained by calibrating the contribution of the filter, which may be the patient, to the apparent source distribution. Photon transmission measurements are made in order to estimate the effect of tissue scattering and absorption or attenuation on radiation source measurements by using a reference source that is external to the patient.

Unfortunately, measuring photon transmission through the body does not duplicate the actual imaging chain acquisition format used in nuclear medicine where photon are transmitted out of the body. Photons in the two instances do not traverse comparable paths.

SUMMARY OF THE INVENTION

In accordance with the present invention, a radiation detection apparatus is provided for radiographic imaging and material composition analysis in which the apparatus can dynamically configure its array geometry and radiation detector parameters for a specific imaging task or it can use an existing radiation detection geometry and settings. This invention is particularly suited for x-ray and gamma ray imaging in nuclear medicine, including scintimammography, and x-ray radiography, specifically, x-ray mammography. There are several advantages inherent to this invention. Superior detectors in cost-effective formats can be utilized and detectors with different properties, including materials, resolution, response time and noise characteristics, can be used within an array. One or more radiation detectors are incorporated into a detector module and one or more modules make up a detector module array. The detector modules transmit detected photon image data and relevant module parameters to a computer system which utilizes this information to electronically-control the modules and in some cases attached collimators. This system is implemented using detector sub-arrays, comprised of one or more detector modules, and detector arrays in order to enhance image quality or analysis capability. Conventional attenuating or rigid geometry collimators, including ones characterized by coded apertures, and unconventional, including x-ray optic, configurable (adaptive), and Compton scatter module, collimators can be employed to improve the energy and/or spatial resolution for the photon radiation detection system. In a similar manner additional types of radiation optic collimators such as neutron optic collimators or electron optic collimators capable of focusing electric or magnetic fields, can be used with neutrons or charged particles, respectively.

In a preferred embodiment semiconductor detectors with appropriate geometries, such as edge-on detectors; thick, linear array detectors; or small, thick, 2-D array detectors, are incorporated into detector modules which are mounted within a frame and configured as an array of detector modules. Detector modules contain one or more detectors, possibly with different properties. A detector array contains one or more modules or types of modules. For nuclear medicine imaging applications detector sub-arrays, comprised of one or more modules, or the entire detector array can be positioned and oriented with respect to the radiation source by an operator or by direct computer control. Collimators and shielding can be attached to or integrated into the module, including interfacing with module electronics if appropriate. Modules communicate with the computer system which monitor and control module and collimator parameters and collect and process radiation data recorded by the detectors. Modules may communicate directly or through a shared network with the computer system. Computer-controlled services include sending electronic instructions to the module mounting hardware, the module, and the collimators, if appropriate. Electronic instructions can initiate actions such as detector array motion, adjustment of the relative position or orientation of one module with respect to other modules, manipulation of a collimator, and the modification of module operating parameters, such as detector signal amplification, filtering, resolution, temperature, operating voltage or sampling rate. Since positioning machinery can be incorporated into the module, actuators can be employed to adjust the position and orientation of the detector. The actuators can also manipulate the positions and orientations of appropriate collimators. A novel collimator design utilizes actuators to alter the configuration of a collimator. The computer-based monitor and control capabilities can be used to track and adjust the locations of modules while they are in motion. Positions, orientations, and motion of all detectors and relevant collimators are recorded and updated as needed throughout the image acquisition process.

A typical nuclear medicine imaging session begins with an operator selecting from a computer display menu a specific detection system with pre-defined array geometry, collimator, and module settings appropriate for the desired imaging task. The detector array configuration can already exist or it can be set up by the computer system. Once a baseline detection system is established, an operator can then adjust and fine tune the detector array position and settings or leave the detector array adjustments and tuning under computer control. While under computer control electronic instructions can be issued dynamically in response to detector module parameter values and detected radiation data that is transferred to the computer system for processing, display, and storage during image acquisition or adaptive imaging. Electronic commands can be used to control the array geometry and motion, detector module parameters, and some types of collimators. Thus an information feedback loop can be implemented as a means of tuning detection system parameters. For some imaging or analysis applications it will be sufficient to configure the detector array based on either a standard geometry, such as line, plane, open box, wedge, ring, cylinder, ellipse, ellipsoid, or sphere, or a contoured geometry, in order to compensate for the radionuclide distribution within the subject and/or the shape of the subject at the region of interest. For example, configurations may be based on the breast size of a woman or on the head size, waist size, or chest size of an adult, child, or infant. A versatile design allows at least a subset of these detector array geometries to be generated "on the fly". A less-versatile design still utilizes modules, but the modules are fixed within a specific detector array geometry or they are constrained to move to specific positions, for example, along a track, within a specific detector array geometry. Less-versatile designs reduce the mechanical complexity of the detection system and may be sufficient for specific imaging tasks. An optional capability is to allow the entire array to undergo discrete or uniform motion. The simplest example of this capability would be to scan a radiation source with a detector array comprised of a single detector module.

In another embodiment, semiconductor detectors are replaced by other types of suitable detectors, such as scintillation detectors, gas detectors, liquid detectors, or superconducting detectors.

In another embodiment reference sources are introduced into the subject and then imaged. The size, shape, intensity, and emission spectrum of the reference sources are known. This allows measurements to be made of photon attenuation due to material in the photon path prior to reaching the detector. This information can be used to estimate the true source distribution from measurements of the apparent source distribution made during image acquisition in a nuclear medicine test. The reference source can also be used to focus the detector array in order to tune the imaging chain.

In another embodiment detector modules and collimators are incorporated into x-ray radiography slit scan imaging systems. X-ray optic collimators can be used to increase the intensity and modify the spectrum of the x-ray radiation that is recorded by the detector module. A single x-ray source is combined with a x-ray optic collimator and a x-ray detector module and used for a x-ray mammography slit scan system. Another improvement involves aggressively compressing sections of the breast and acquiring separate images of the highly-compressed sections rather than acquiring a single image of the entire, mildly-compressed breast.

The system of the present invention may utilize devices detailed in prior inventions for slit-scan or slot-scan radiographic x-ray imaging in which photons are detected directly using edge-on array detectors; small, 2-D semiconductor array detectors; or semiconductor array detectors coupled to scintillators. This new device can also use thick, linear semiconductor array detectors and thick, small, 2-D semiconductor array detectors in addition to other types of detectors. Manufacturing costs for these detectors are much less than those associated with large-area or moderate-area, thick, planar, 2-D semiconductor array detectors made from materials such as, but not limited to, CdZnTe, CdTe, GaAs, Ge, Si, SiC, or HgI2. The detector format is also compatible with detectors such as thin, linear semiconductor arrays or thin, small, 2-D semiconductor arrays coupled to scintillators. For example, thin, linear semiconductor arrays of avalanche photodiodes coupled to scintillators can be used as radiation detectors. This approach can be extended to include scintillators coupled to integrated photoemissive cathodes or small PMTs; small, gas microcapillary detector assemblies; or small superconducting array detectors. Consider a scenario in which radiation is incident upon a planar edge-on detector. The detector thickness (height) now defines the maximum detector entrance aperture while the length or width of the detector area now defines the maximum attenuation distance for edge-on radiation detector designs including semiconductor drift chamber, single-sided strip, and double-sided strip detectors, including micro-strip detector versions. Strip widths can be tapered or curved, in the case of drift chamber detectors, if focusing is desired. In the case of double-sided parallel strip detectors in which opposing strips are parallel, both electrons and holes can be collected to provide 2-D position information across the aperture. If strips on one side run perpendicular to those on the other side, then depth-of-interaction information can be obtained. If strips are segmented in either a single-sided or double-sided parallel strip detector then depth-of-interaction information can be obtained and readout rates can be improved.

These and other advantages of the present invention will become apparent upon reference to the accompanying drawings and the following description.

BRIEF DESCRIPTION OF THE DRAWINGS

FIGS. 5a(i)–(ii) illustrate a configurable dual x-ray refractive lens.

DETAILED DESCRIPTION

General Detector Array

Figure 1:
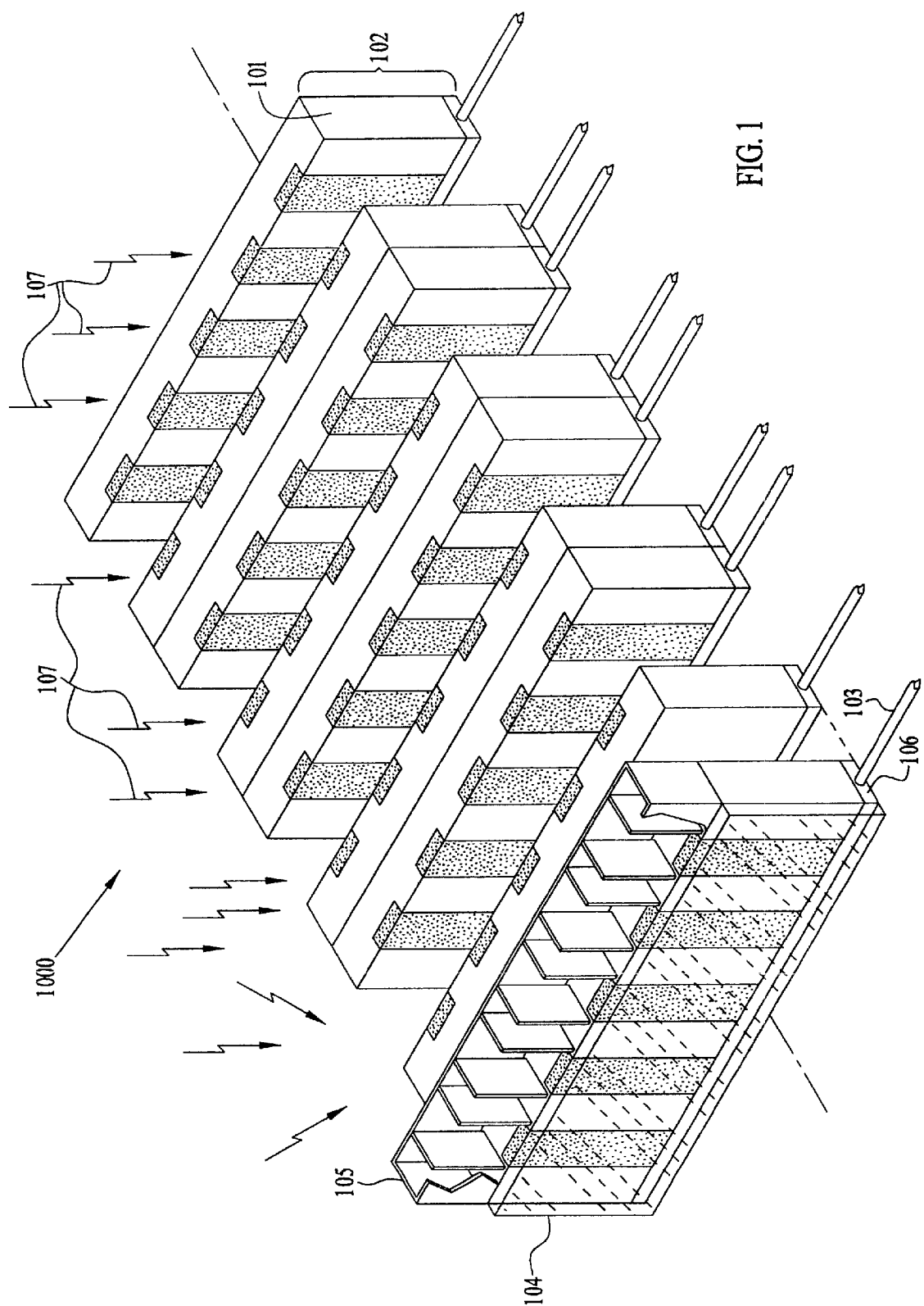
FIG. 1 illustrates a perspective view of a detector module array.

In one embodiment of the present invention, as illustrated in FIG. 1, a detector array 1000 preferably incorporates separate, discrete detector modules 102, illustrated here as edge-on or strip/micro-strip detectors, configured in a planar geometry to optimize the detection of incident radiation 107. The detector array 1000 may be utilized as part of a gamma camera. Currently, gamma cameras are not based on detector arrays such as detector array 1000 which incorporates discrete modules 102.

Detector modules 102 utilize one or more detectors 101, typically array detectors, which can have different properties. Note that several of the modules 102 include more than one detector. Additionally, linear array or small, 2-D array semiconductor detectors may be incorporated into the detector modules 102. Each module 102 also includes a base 106 and a communications link 103.

The base 106 preferably contains detector electronics, power management components, temperature control components, and a data or information channel for communicating with the computer system. The base 106 may also incorporate a module electronic readout unit that includes a signal conditioner or filter, an amplifier, an analog-to-digital converter, and a communication interface. Additionally, the detector module 102 may be coupled to an electronically-controlled thermoelectric cooler or other temperature regulating device which resides in the detector module base 106. In this embodiment, the temperature-regulating device provides temperature control for the detector module 102 and its electronic readout unit.

The communications link 103 provides power to the module 102 and connects the base 106 to a computer system.

Through the attachment with the base 106, the link 103 enables a computer system to control the configuration of the module 102. The communication link 103 preferably is used to off-load the digitized detector radiation data to a computer system for analysis and image reconstruction. The computer system, which can include general purpose, dedicated, and embedded computers, provides monitor and control services to modules 102 and to the entire detector array 1000. The computer system evaluates module, detector array parameters, and the detected radiation image data. The detected data is processed and can be displayed and stored if desired. Additional relevant module information, such as temperature, amplifier settings, detector voltages, position, orientation, and motion information, can be transmitted to this computer system over the communication link 103. Alternatively, a separate communication channel may be incorporated to transfer the additional information between the module 102 and the computer. The computer system transmits instructions that update the detector array 1000. This establishes a dynamic information feedback loop that is useful for adaptive imaging.

Each module 102 may optionally have its own radiation shielding 104 and collimator 105 mounted on the wall of the module 102, although only one module is shown with these items for clarity. Module walls are typically thin, which permits radiation-shielding 104 to be attached to the module wall or inserted between adjacent modules 102 when needed. As illustrated in FIG. 1, collimators 105 are placed in operable contact with the detector modules 102. However, the array 1000 is capable of operating without collimators 105. Even in the absence of collimators 105, collimation exists to a limited extent because the modules 102 are discrete and physically separated. In this alternative embodiment, the array 1000 is designed to detect incident radiation 107 using detector modules 102 without attached collimators 105.

Turning back to the embodiment illustrated in FIG. 1, both conventional and unconventional collimators 105 can be attached to the detector module 102. If the collimators 105 are capable of being electronically-controlled to perform mechanical alignment or to manipulate unconventional collimators, then the module 102 may utilize the communications link 103 to provide power management and communication capability to the collimator 105. The communication link 103 is also used to transmit collimator parameters and settings between the module 102 and the computer system.

A detector array 1000 can be comprised of more than one type of detector module 102. A number of array geometries, in addition to the standard planar detector array format, can be utilized. This design may also be implemented by using semiconductor detectors coupled to scintillators as well as other types of detectors. These detectors are described in Nelson, U.S. Pat. No. 4,560,882, which is incorporated by reference for all it discloses and describes. Limiting the focusing of the modules 102 using edge-on strip detectors is possible by tapering the edge-on strips, as described in Nelson, U.S. Pat. No. 4,937,453, filed May 6, 1987, which is hereby incorporated by reference for all it discloses and describes.

The increased detector density is useful for enhancing the imaging of select regions of the subject. For example, the array 1000 illustrated in FIG. 1 is particularly suited to form large area, 2-D detector arrays, such as those described by Nelson, U.S. Pat. No. 4,937,453, due to the close proximity of multiple modules 102.

The detector array 1000 and individual detector modules 102 can be scanned or dithered, i.e. moved repeatedly between adjacent locations, as needed so as to provide appropriate sampling of spatial regions which would otherwise be 'dead areas' due to a lack of detectors at those positions. Scanning motion is suitable for sampling regions that would otherwise require multiple detector modules to fill. Dithering is suitable for sampling regions that are typically less than the size of detector pixels. A detector module 102 can incorporate more than one detector 101 with the same or different properties. A detector array 1000 can use more than one type of detector module 102. For example, detectors 101 or detector modules 102 with different energy resolutions, spatial resolutions, stopping powers, and readout rates can be combined in order to match the imaging characteristics of the device to specific as well as general applications. Temperature management, typically cooling, of the detectors 101 may be utilized as needed. Preferably the detectors 101 will operate at or near room temperature for applications in nuclear medicine, but this may not always be possible. Several safety features can be included with the detector array 1000 to restrict its speed of motion and proximity to the subject. These can include optical and acoustic range sensors as well as pressure-sensing devices. Computer-controlled positioning and sensor devices have been widely used for many years in applications such as medical imaging, robotics, factory automation, precision machine tools, micromachines, and aviation.

An external container (not shown) preferably is typically employed to shield the detector array 1000 and any electronic components from external electromagnetic fields and physical contact.

Specialized Detector Arrays

The present invention includes specialized detector arrays such as those illustrated in FIGS. 2a–2d. FIGS. 2a–2d illustrate perspective views of fixed cylindrical-like (FIG. 2a), spherical-like (FIG. 2b), and wearable (FIG. 2c) detector array geometries.

Cylindrical and Spherical Detector Arrays

Figure 2A:
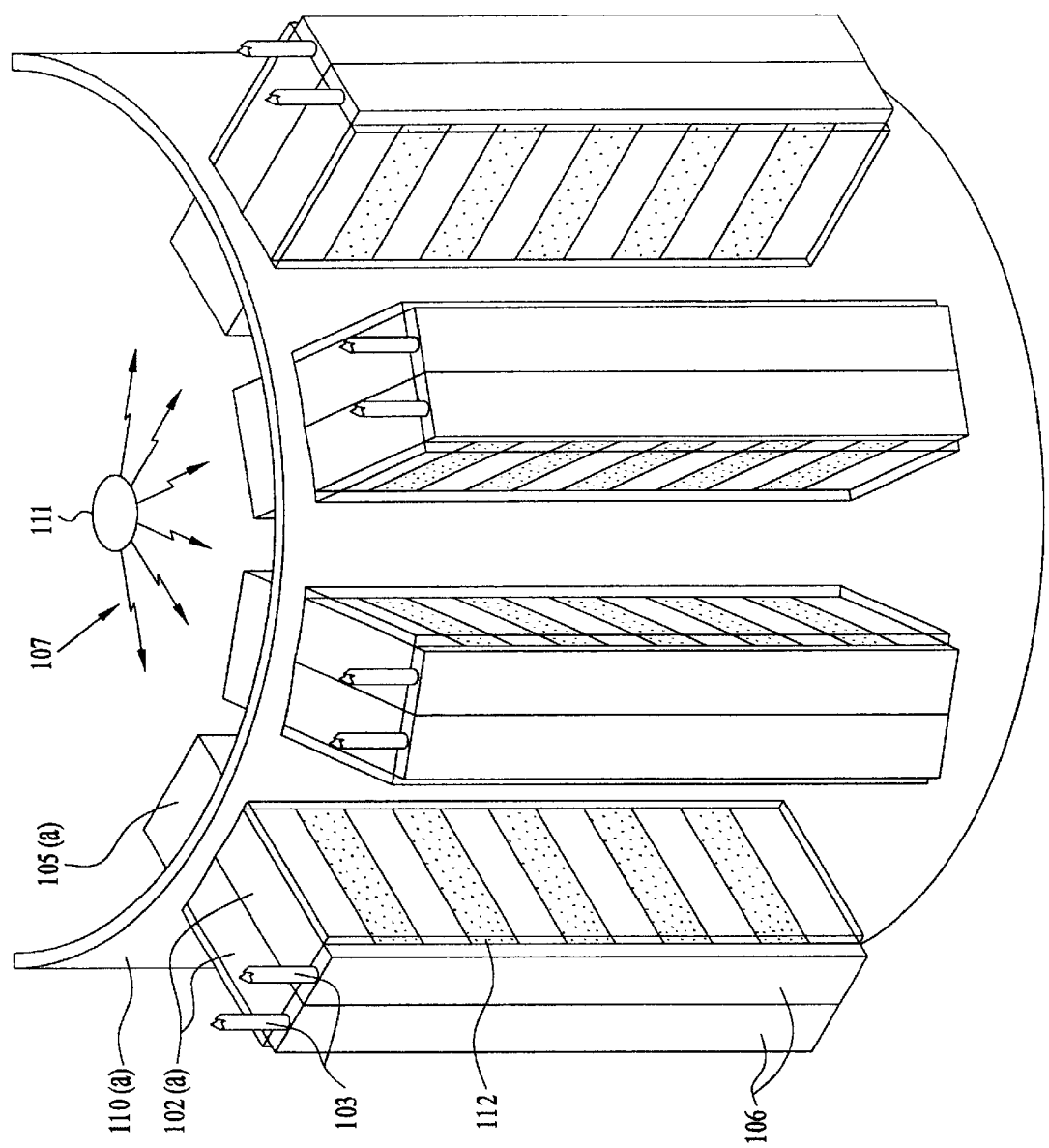
FIGS. 2a–2c and 2d(i)–(iii) illustrate perspective views of various cylindrical, spherical and wearable detector array geometries.
Figure 2B:
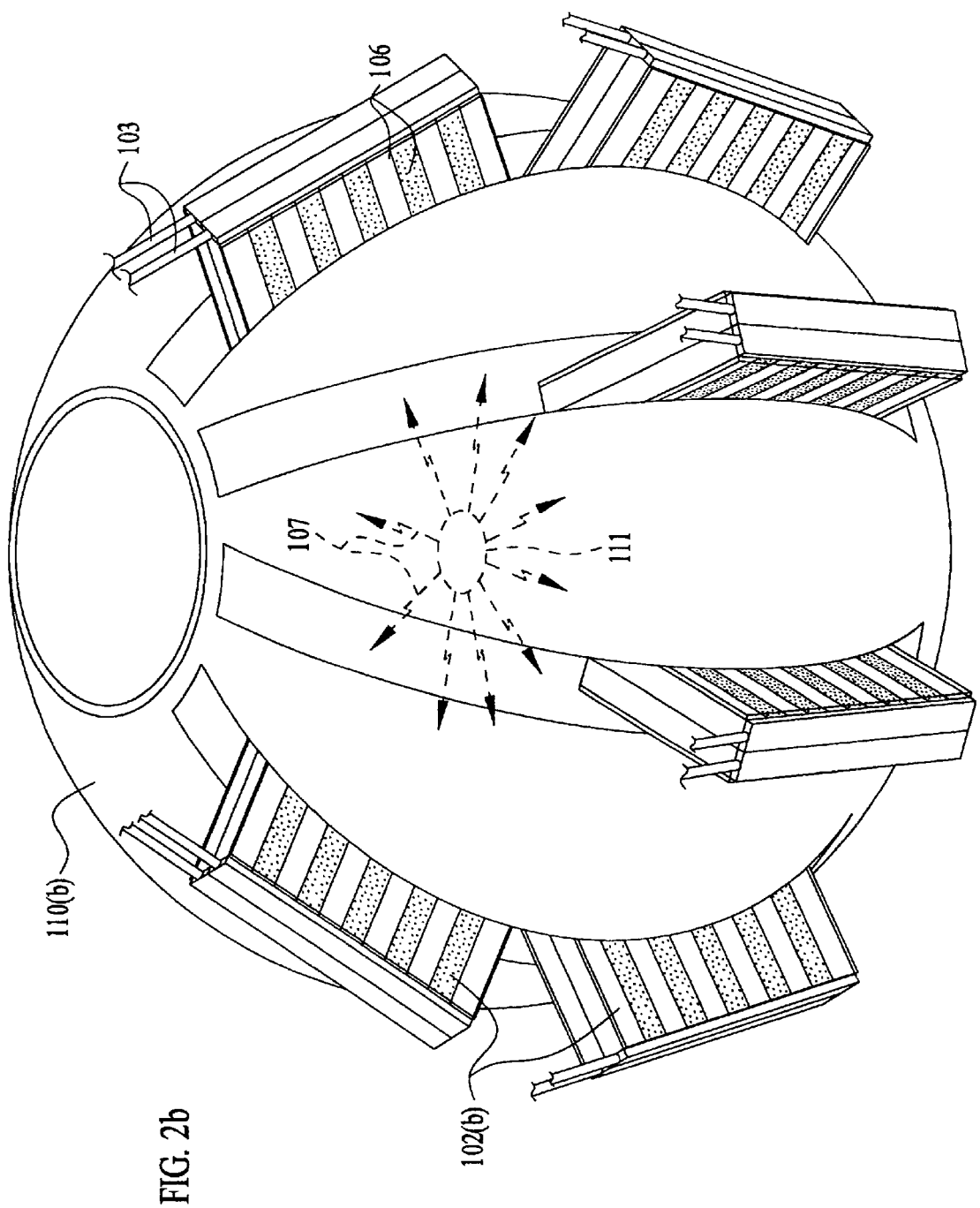

In FIGS. 2a and 2b, edge-on detector modules, 102(a) and 102(b), are capable of motion along tracks, 110(a) and 110(b). Such a characteristic enables the modules 102(a) and 102(b) to sample gaps between individual modules. Turning to FIG. 2a, the modules 102(a) are shown with side shielding 112 and a radiation source 111. The shielding 112 may be included on the modules 102(a) in order to minimize the detection of radiation escaping from neighboring detectors. The modules 102(a) are configured to move in a cylindrical fashion along the tracks 110(a).

Turning to FIG. 2b, the tracks 110(b) are configured to allow the modules 102(b) to move in a spherical motion with both up and down and side to side directionality possible. In both FIG. 2a and FIG. 2b, the modules, 102(a) and 102(b), move independently along tracks, 110(a) and 110(b), as part of a detector array or detector sub-array, or both types of motion can be executed in order to improve the sampling uniformity of the subject. The optional use of a flexible track (not shown) permits the detector modules, 102(a) and 102(b), to follow the contours of the subject more closely by enabling the modules, 102(a) and 102(b), to move in conformity with the subject. Using a flexible track would allow for a contoured geometry.

The computer system keeps a chronological, real time record of module and array parameters, including position and orientation of detectors and collimators, motion, detector amplification and noise, during image acquisition and during detector array calibration.

Detector array configurations such as those shown in FIG. 2a and FIG. 2b may be extended or filled-out to form a more complete cylinder, such as a ring shape, or even spherical arrays of detectors. Detector array configurations may also be shaped to fit other standard geometries, including slit, slot, line, plane, open box, wedge, ellipse, ellipsoid, or a combination of geometries. Collimators can be employed with individual edge-on detectors, such as illustrated in FIG. 1.

Wearable Detector Arrays

Figure 2C:
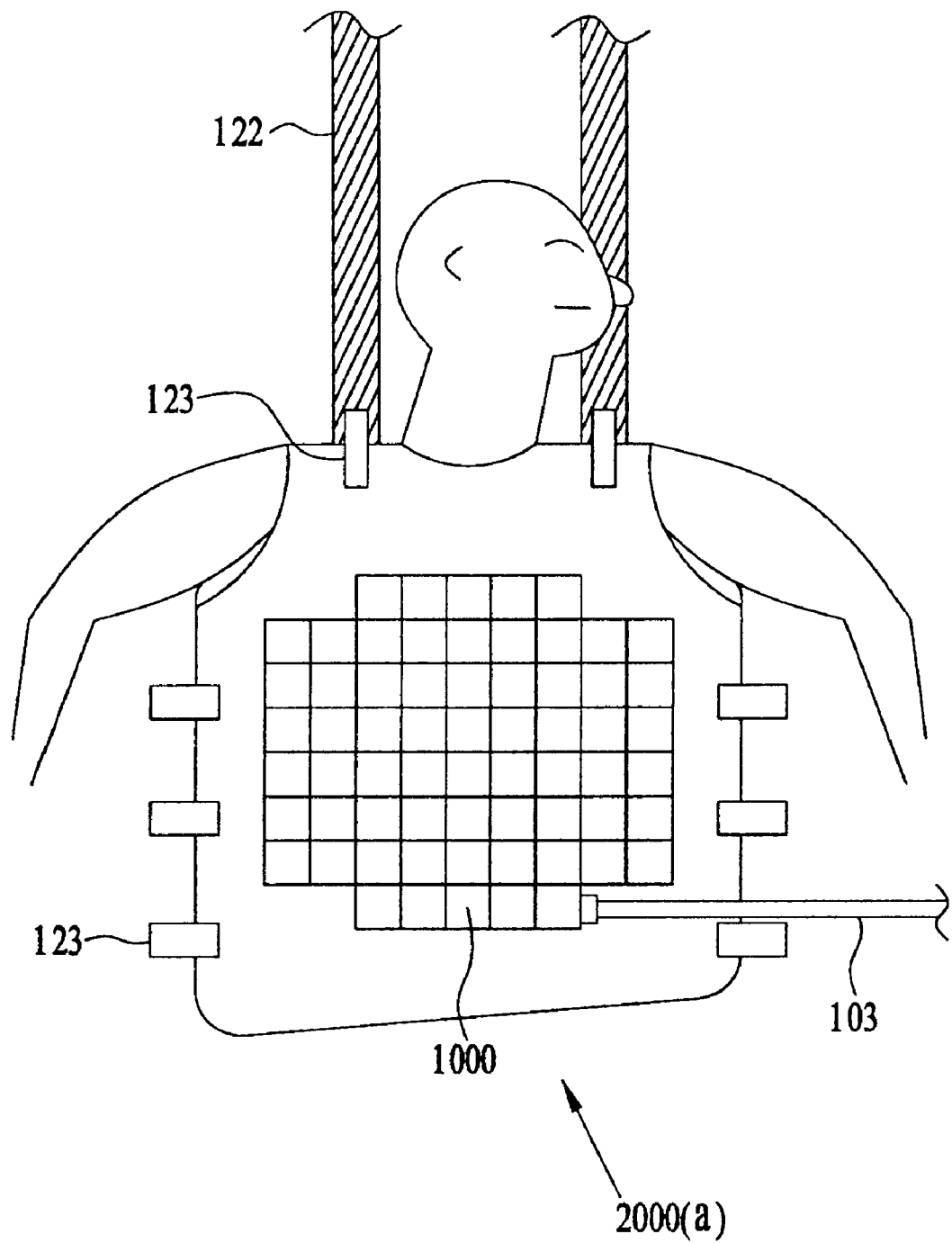

Turning now to FIG. 2c, a wearable detector array 2000 (*a*) in the form of a detector vest, similar in form to an upper torso "body armor" shell, a down-filled winter vest, or a breastplate, is illustrated. The detector vest 2000(*a*) is designed such that it approximately conforms to the shape of the patient. Straps 123 may be included to allow the patient to securely wear the detector vest 2000(*a*). Straps 123 may also be used with other wearable detector arrays. For example, a wearable helmet could incorporate an adjustable chinstrap. The adjustable straps 123 also permit the detector vest 2000(*a*) to be positioned at the desired location for a range of body types.

A detector array 1000, sufficient in size for imaging the heart, is incorporated into the detector vest 2000(*a*). This configuration can be cost-effective for particular cardiac imaging studies since the area of the detector array, and any attached collimators, is not much larger than the projected area of the heart onto the plane of the detector array. An additional benefit is the reduction in weight that is possible by employing a small detector array and collimator. A detector vest 2000(*a*) such as that illustrated in FIG. 2c enables effective sampling of the region of interest throughout the examination, mitigating problems due to undesired patient motion. Wearable detector devices may also permit claustrophobic patients to undergo testing since one or multiple large gamma camera heads will not be positioned about the patient so as to create a confining effect. Communication links 103 are used to facilitate communication between the detector array 1000 and a computer and to supply power to the detector modules 102.

An optional support harness 122 reduces the additional stress imposed upon the patient that may be generated due to the weight and bulk of the detector vest 2000(*a*). If the detector vest 2000(*a*) is too heavy or bulky for the patient then a flexible suspension system using the support harness 122 is employed to provide at least partial support for the detector vest 2000(*a*). The use of a support harness 122 is very similar to the concept of using a training harness for a patient or animal recovering from injuries or for simulating effects such as reduced gravity for an astronaut. A flexible suspension system can also be employed with other wearable detector devices if needed.

An alternate implementation of a wearable detector which still permits limited mobility is a detector array configuration that is supported by a stand with adjustments for height, tilt, and rotation. The patient presses the appropriate body part (head, neck, chest, stomach, etc.) against the detector array configuration while stationary or performing an exercise regimen. This imaging format maintains a reasonable alignment between the detector array and body region and is similar in principle to using exercise equipment such as cross-country ski trainers where an individual presses the hips or stomach against an adjustable pad.

Figure 2D:
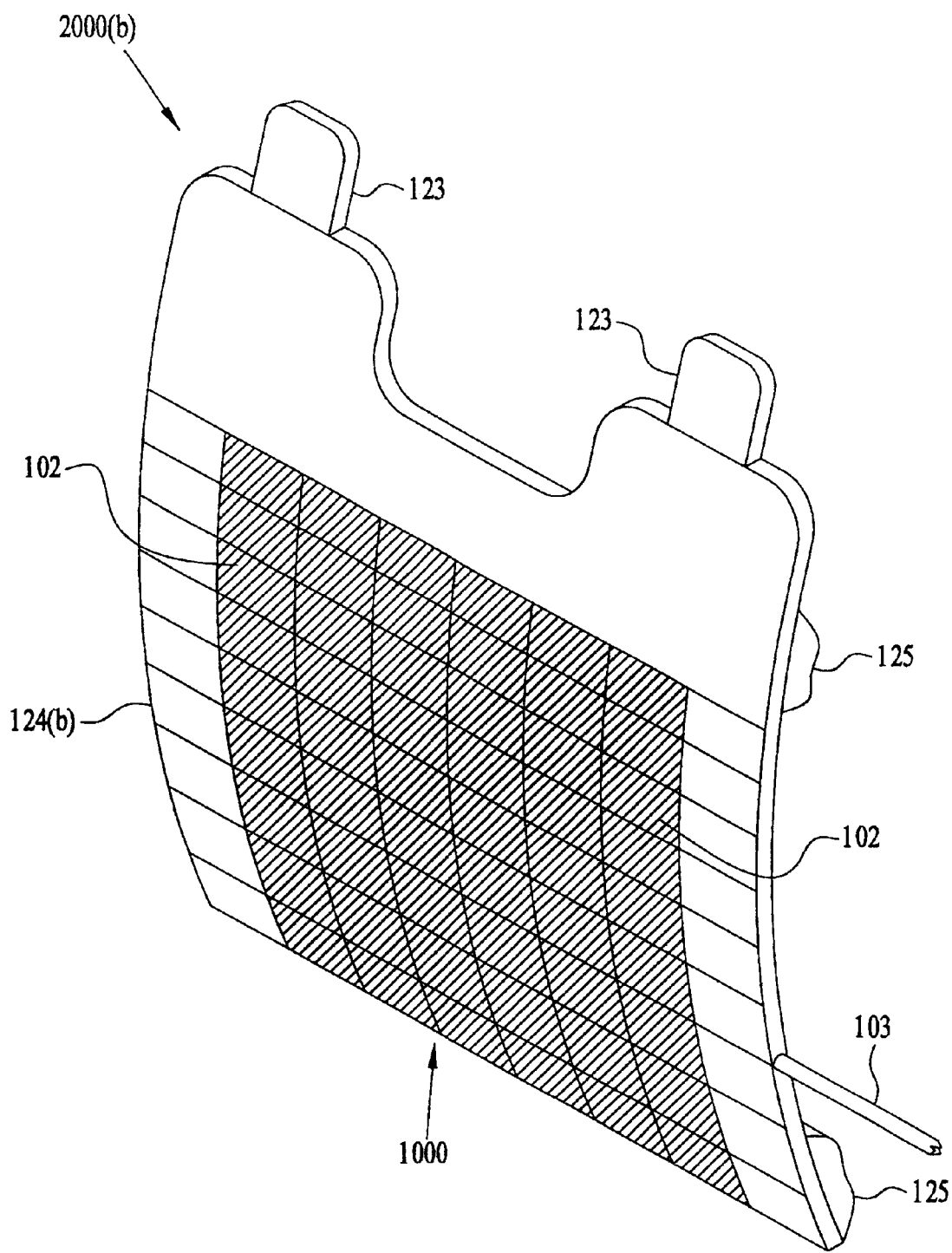

Detector arrays can be incorporated into similar equipment to create wearable detector arrays such as wearable detector helmets/head gear, detector neck braces, detector brassieres, and detector belts or girdles. FIGS. 2*d*(i)–2*d*(iii) illustrate different wearable devices, namely a detector vest (2000(*b*), FIG. 2*d*(i)), a detector helmet (2000(*c*), FIG. 2*d*(ii)), and a detector brassiere (2000(*d*), FIG. 2*d*(iii)), that use open frames, 124(*b*)–124(*d*), in the shape of the desired geometry for mounting detector modules and collimators. The open frames 124(*b*)–124(*d*) provide a grid for mounting the detector array 1000 and any associated collimators to examine different sections of the subject. For example, a detector array 1000 could be mounted on an open frame detector vest 2000(*b*) so as to image the heart and lungs and another detector array 1000, possibly with modules 102 of different properties and collimators 105, could be mounted so as to image the kidneys and gall bladder. The many possible configurations of detector arrays 1000 that can be implemented in a wearable device such as a wearable detector vest enable it to provide the same types of views, including 180 degrees, 240 degrees, and 360 degrees, which single and multiple head Gamma cameras are able to acquire.

Additionally, compressible pieces of foam or other expandable bladders 125 may also be attached inside a wearable detector in order to allow for a further customized fit to the patient. Bladders 125 are also utilized to minimize contact between the patient's body and rigid areas of the wearable detector, including the detector array 1000 with detector modules 102 and collimators 105. The bladders 125 are directly comparable to the use of foam and expandable bladders in athletic gear such as football helmets. If the pressure exerted by an expandable bladder 125 is modulated, an established technique that is used to assist circulation in the legs of bed-ridden patients, then specific physiological studies that depend on circulation, including breast physiology, can also be conducted.

If needed, the patient can be cooled by circulating air or a contained liquid between regions of the wearable detector and the patient's body that do not interfere with image acquisition. The power and communication connections, such as the communications links 103, that interact with the detector arrays 1000 can also interact with or control cooling devices (not shown) and expandable bladders 125.

Detector arrays 1000 are capable of being installed in fixed configurations in wearable detectors or they can be designed to be removable. For example, removable detector arrays 1000 may be configured to snap into pre-defined positions, dynamically establishing power and communication connections with the power source and computer, respectively, and permitting customization. The locations of the detector arrays 1000, and modules 102 within the array 1000, on the wearable device are transmitted to a computer that communicates with each detector module 102, as in the case of the other detector array geometries already discussed. Wearable detectors may be of particular value in situations where involuntary or required patient motion degrades image quality. For example, a patient could wear a detector vest 2000(*a*) or an open frame detector vest 2000(*b*) while undergoing a treadmill cardiac stress test. Instead of the patient trying to maintain the same position with respect to the detector vest, 2000(*a*) or 2000(*b*), the detector vest 2000(*a*) or 2000(*b*) remains aligned with the patient. A patient can also wear the detector vest 2000(*a*) or 2000(*b*) while lying down or riding a stationary bike. The ability to utilize detector arrays in situations where involuntary or required patient motion may occur also applies to wearable detectors other than detector vests (2000(*a*) or 2000(*b*)), including helmets 2000(*c*), neck braces or neck wraps (not shown), brassieres 2000(*d*), and belts/girdles (not shown).

A wearable detector may allow multiple studies, using multiple radionuclide tracers and appropriate detector energy windows, to be conducted at one time. For example, thallium, technetium 99 m, and a positron emitter used together could permit metabolism, regional blood flow, perfusion abnormalities, and ventricular function to be studied while exercising.

Configurable Detector Arrays

Figure 3B:
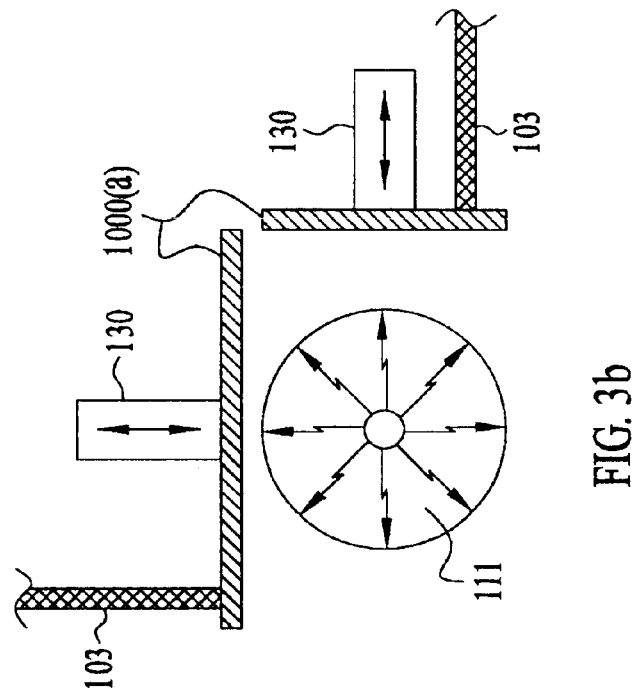
FIG. 3b illustrates an L-shaped detector array configuration.
Figure 3A:
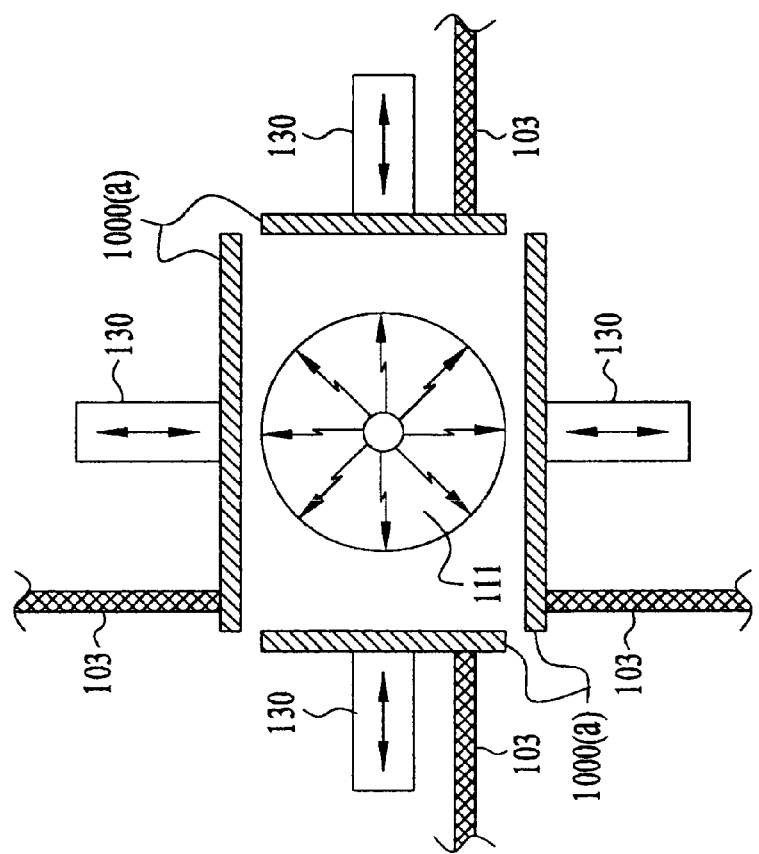
FIG. 3a illustrates perspective views of box-shaped implementations of detector arrays.

Turning to FIGS. 3a–3d, movable detector arrays are illustrated. When a detection system involves movable detector arrays 1000(a), the motion of the detector arrays 1000(a), or the detector modules 102, do not have to be confined to a track. Another implementation of the detection system permits the detector array 1000(a) to move as a unit, but the modules 102 within the array can still be positioned independently. This allows the array 1000(a) of detector modules 102 to be refocused or individual detector modules 102, as well as the radiation detectors 101 incorporated into those modules 102, to be repositioned as required in order to optimize detection for a specific type and distribution of radionuclide. For example, a detector array 1000(a) of fixed or limited configurability can be used in a plane, "L" (FIG. 3b), or open box (FIG. 3a) geometry. FIG. 3a shows perspective views of "box"-shaped implementations of detector arrays 1000(a) for imaging the heart. Simple versions include standard geometries that are somewhat fixed. In this example, variants of a rectangular shape are possible. Detector arrays 1000(a) are present on two/"L"-shaped (FIG. 3b), three (not shown), or four (FIG. 3a) sides of the subject. Each detector array 1000(a) is positioned by an electronically controlled actuator arm 130.

Figure 3D:
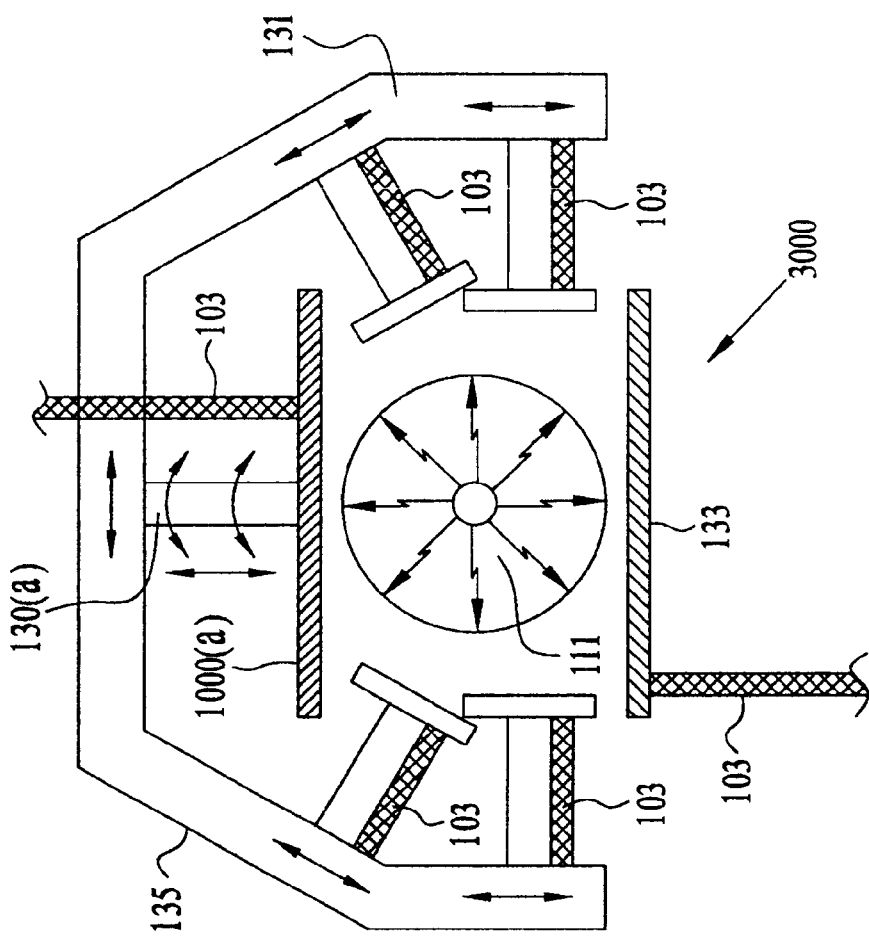
FIGS. 3d–3f illustrate configurable arrays operated by actuator arms.
Figure 3C:
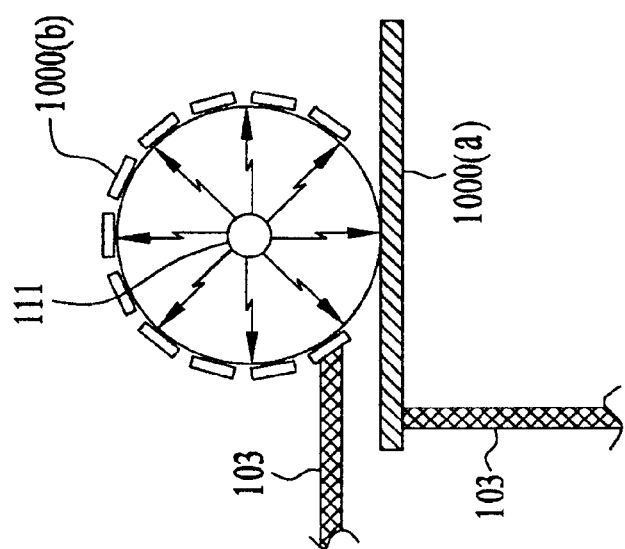
FIG. 3c illustrates a compliant detector array configuration.

Turning to FIG. 3c, a compliant detector array 1000(b) is shown. The compliant detector array 1000(b) is comprised of detector modules 102 that are small in size, offering more orientation and positioning options. The compliant detector array 1000(b) enables the array 1000(b) to follow the approximate contour of the region of interest, as shown in FIG. 3c, thereby allowing for a contoured geometry for the array 1000(b). Positioning may also be accomplished with or without the aid of actuator arms 30. As illustrated in FIG. 3c, the flat side of the subject may be positioned immediately next to a conventional, planar detector array 1000 so that the system does not require an actuator arm.

A gantry that would normally be used for encircling the subject is not necessary in this embodiment since the flat side of the subject can be positioned next to the planar detector array 1000. The computer system monitors and records in real time the position and orientation of the detector arrays 1000 and 1000(b), including detectors modules 102, detectors 101, and collimators 105, and relevant motions with respect to the subject.

FIG. 3d illustrates a configurable detector system 3000 that utilizes configurable arrays 1000(a) manipulated by computer-controlled actuator arms 130. The actuator arms 130 are able to move along slides or rails 131 within a gantry 135, thereby allowing the detector system 3000 to be reconfigured "on the fly". The actuator arms 130(a) are more flexible than the actuator arms 130 shown in FIGS. 3a and 3b due to the inclusion of rotation capability. The lower detector module array 133 is shown as stationary since the subject is positioned next to it in this configuration. Actuator control of the lower detector module array 133 may be implemented if desired, thereby allowing dynamic position of the lower detector array 133 in the same manner as the other detector arrays 1000(a) illustrated. Position and orientation information of any of the detector arrays 1000(a), 133 with respect to the subject is recorded.

Figure 3E:
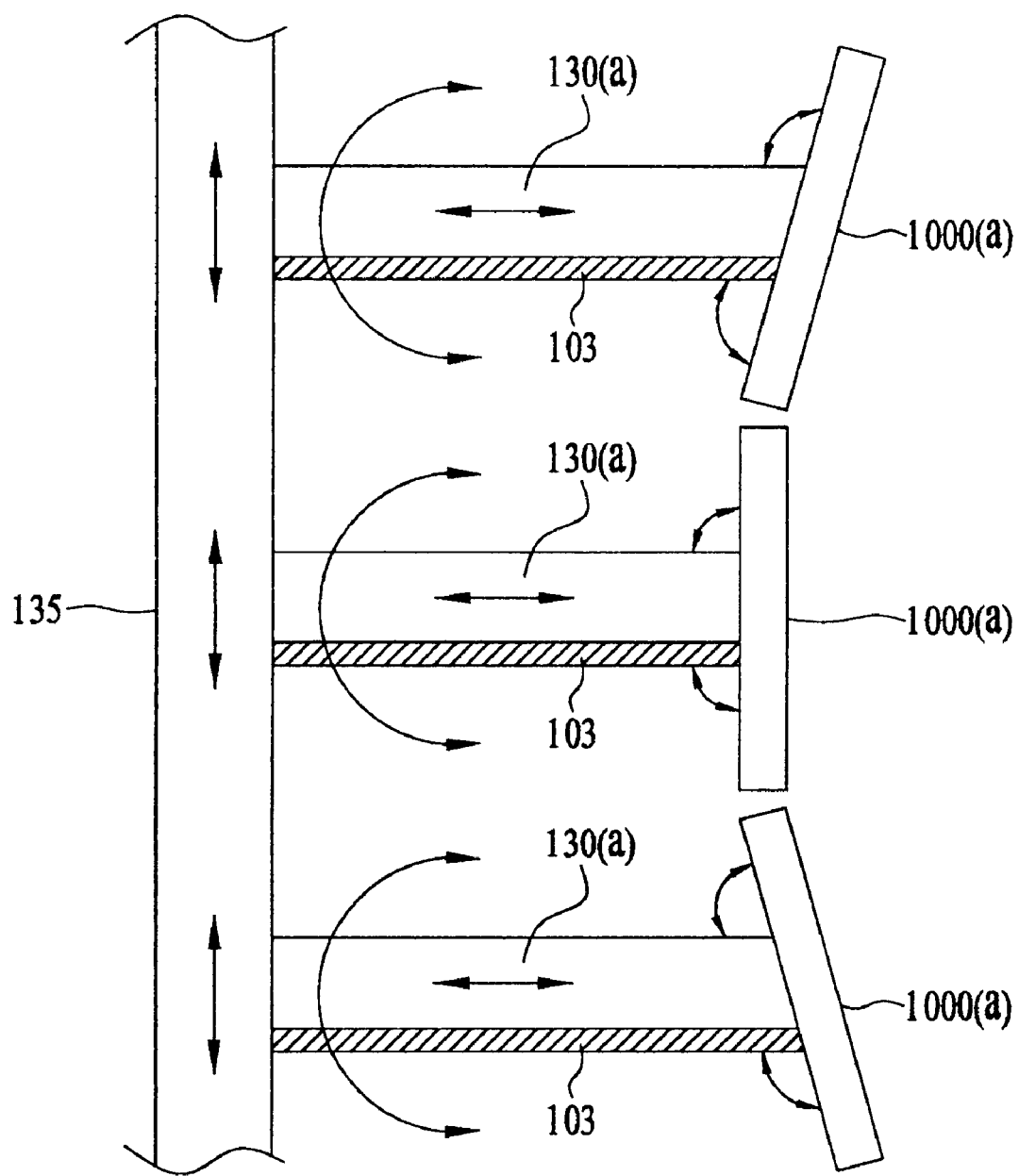

FIG. 3e illustrates one example of configurable arrays 1000(a) mounted on actuator arms 130(a) that are capable of rotational motion and additionally capable of tilting the arrays 1000(a). The ability to tilt the arrays 1000(a) with respect to the actuator arms 130(a) makes the arrays 1000(a) adaptable to a greater range of patient geometries. The overlap between detector arrays 1000(a) is reduced providing each array 1000(a) with its own actuator arm 130(a), thereby enabling the movement of each array 1000(a) independently of the other arrays 1000(a). The actuator arms 130(a) preferably are capable of bidirectional movement along a gantry 135. Communications links 103 enables a computer system to control the actuator arms and the positioning of the arrays 1000(a).

Figure 3F:
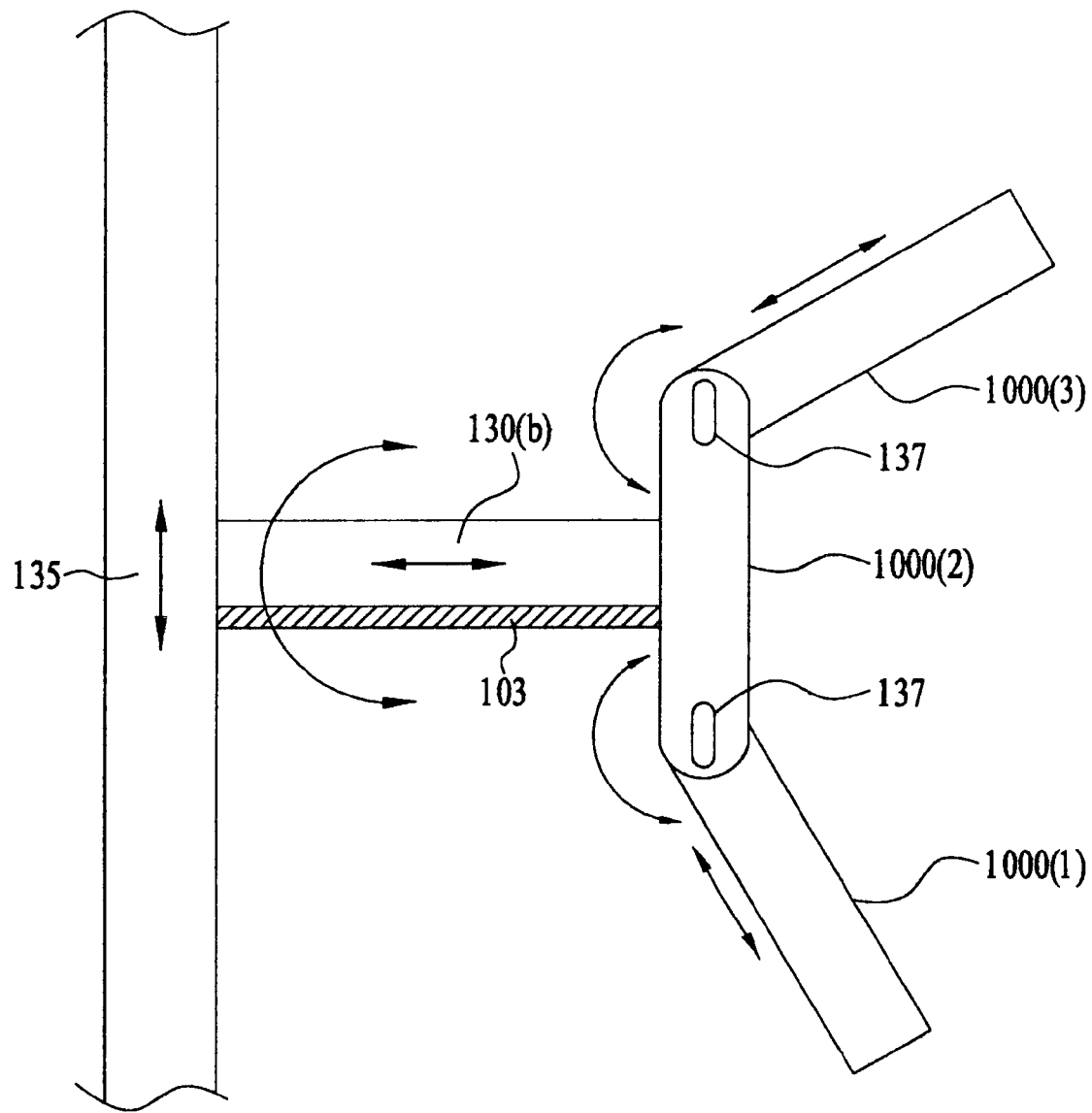

Alternatively, as illustrated in FIG. 3f, three detector arrays 1000(1)–(3) may be joined in operable connection with each other with only one of the arrays 1000(2) attached to the actuator arm 130(b). The arrays 1000(1)–(3) are connected such that a middle array 1000(2) is connected on each end of the array 1000(2) to one end of the other arrays 1000(1), 1000(3). The arrays 1000(1)–(3) are connected by hinges 137 that enable arrays 1000(1) and 1000(3) to be tilted relative to array 1000(2). The hinges 137 preferably are configured such that the arrays 1000(1) and 1000(3) are able to move in a bilateral direction away from and towards the middle array 1000(2) while also being able to tilt relative to the middle array 1000(2). The middle array 1000(2) is additionally in operable connection with the distal end of the actuator arm 130(b). As with the embodiment illustrated in FIG. 3e, the actuator arm 130(b) is preferably capable of bidirectional movement along a gantry 135. A communications link 103 is provided that enables a computer system to control the movement of the actuator arm 130(b) and the arrays 1000(1), 1000(2), and 1000(3). Additionally, arrays 1000(1) and 1000(3) are able to be positioned manually rather than solely by computer remote control.

Unconventional Collimators

Figure 4A:
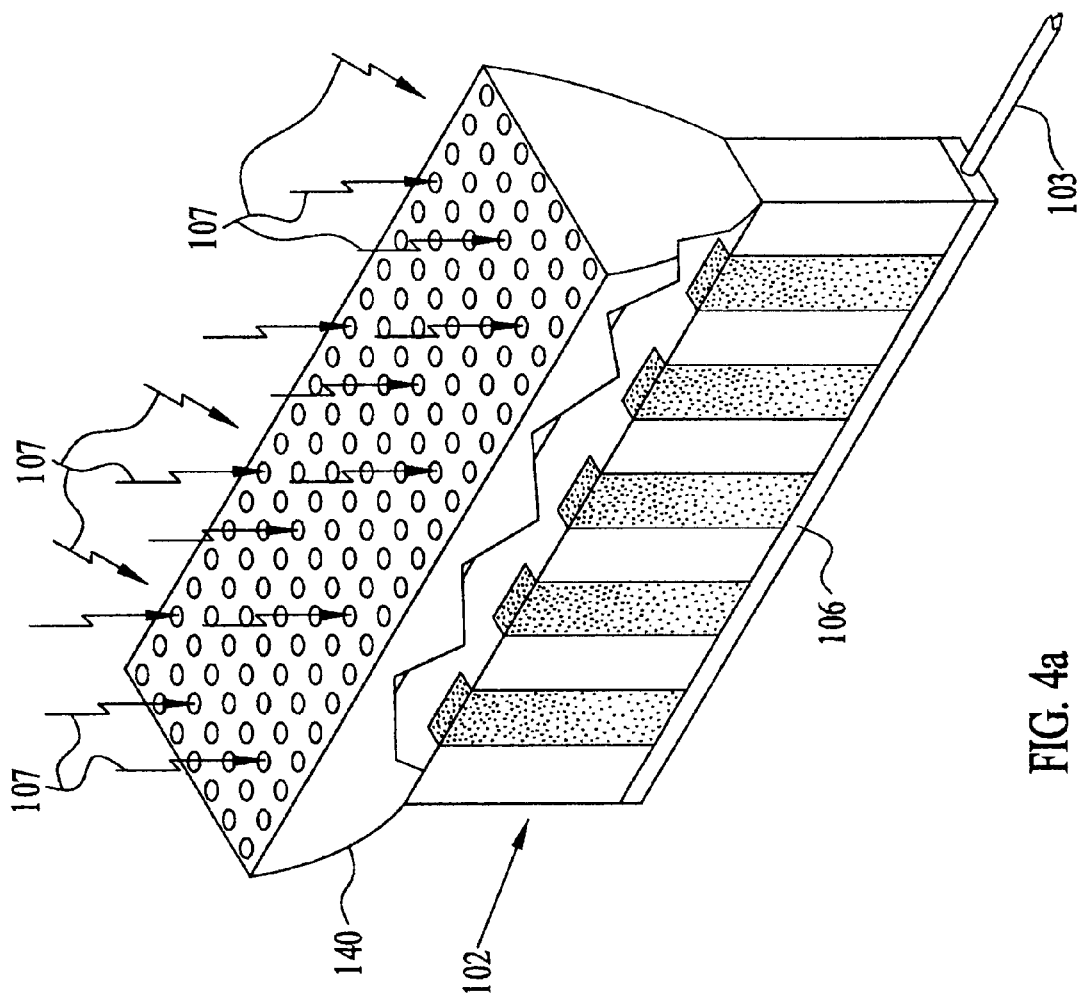
FIGS. 4a–4b illustrate perspective views of an edge-on detector module with an unconventional minifying/tapered capillary x-ray optic collimator.
Figure 4B:
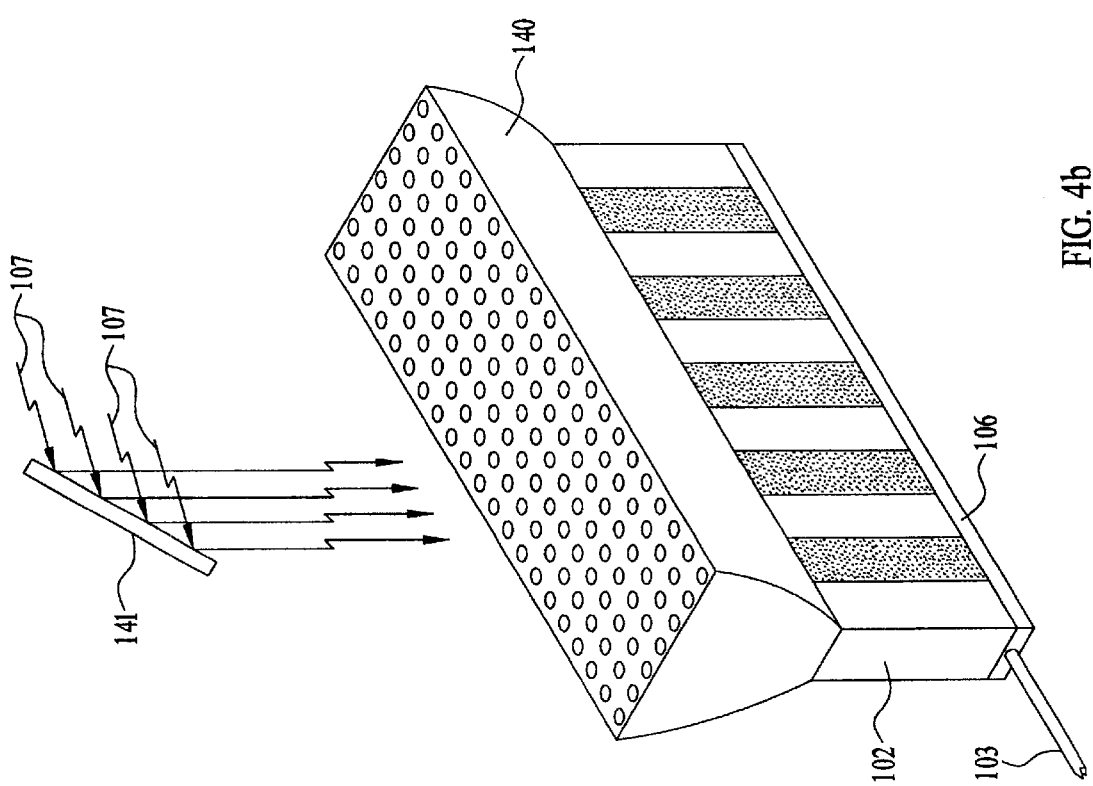

Turning to FIG. 4a, a perspective, frontal view of an edge-on detector module 102 with an unconventional minifying or tapered capillary x-ray optic collimator 140 is shown. This collimator 140 has increased the apparent aperture of the detector module 102, thereby enabling the detector module 102 to detect a larger proportion of the source radiation. Additionally, the detection of scattered or non-directional photons are decreased. The collimator 140 output face, or aperture, is closely matched to the actual detector aperture. This configuration allows for the design of the module 102 to remain compact. FIG. 4b shows a side view of the same detector module 102 with a minifying capillary x-ray optic collimator 140. Additionally, an optional configurable x-ray optic collimator 141, which is a configurable multilayer x-ray mirror that functions as a narrow bandwidth and directional filter, is introduced.

Conventional, including coded apertures, collimators and unconventional collimators can be used with the present invention. Typical conventional attenuating, rigid geometry collimating devices range from simple pinholes and slats or septa to focused and unfocused grids. Unconventional collimating devices include x-ray optics, configurable collimators, and Compton scatter module collimators. Cost and imaging requirements, including types of detectors, spatial resolution, radiation energies, size of subject, and source distribution and intensity, will influence the selection of collimators. Examples of x-ray optics include devices such as x-ray mirrors, Bragg crystals, pyrolitic graphite crystals such as those described in Nelson et al., U.S. Pat. No. 4,958,363, filed Aug. 12, 1988, and Nelson et al., U.S. Pat. No. 4,969,175, filed May 10, 1989, which are hereby incorporated by reference for all they disclose and describe, capillary x-ray optics, refractive x-ray lenses, diffractive x-ray lenses and structures, and x-ray Fresnel lenses. If the x-ray optic device or collimator has the ability to focus radiation then it may be used to expand the apparent aperture of the detector, as shown in the module 102 illustrated in FIG. 4a, thereby making more efficient use of the radiation source. Minifying capillary x-ray lenses, refractive x-ray lenses, diffractive x-ray lenses and structures, curved x-ray mirrors, and x-ray zone plates are examples of focusing x-ray optic devices. For typical nuclear medicine applications the x-ray optic collimator may be integrated with the detector module 102, as in FIG. 4a, or held in a separate frame and then aligned with a detector module 102, as in FIG. 5b(ii).

Figure 5B:
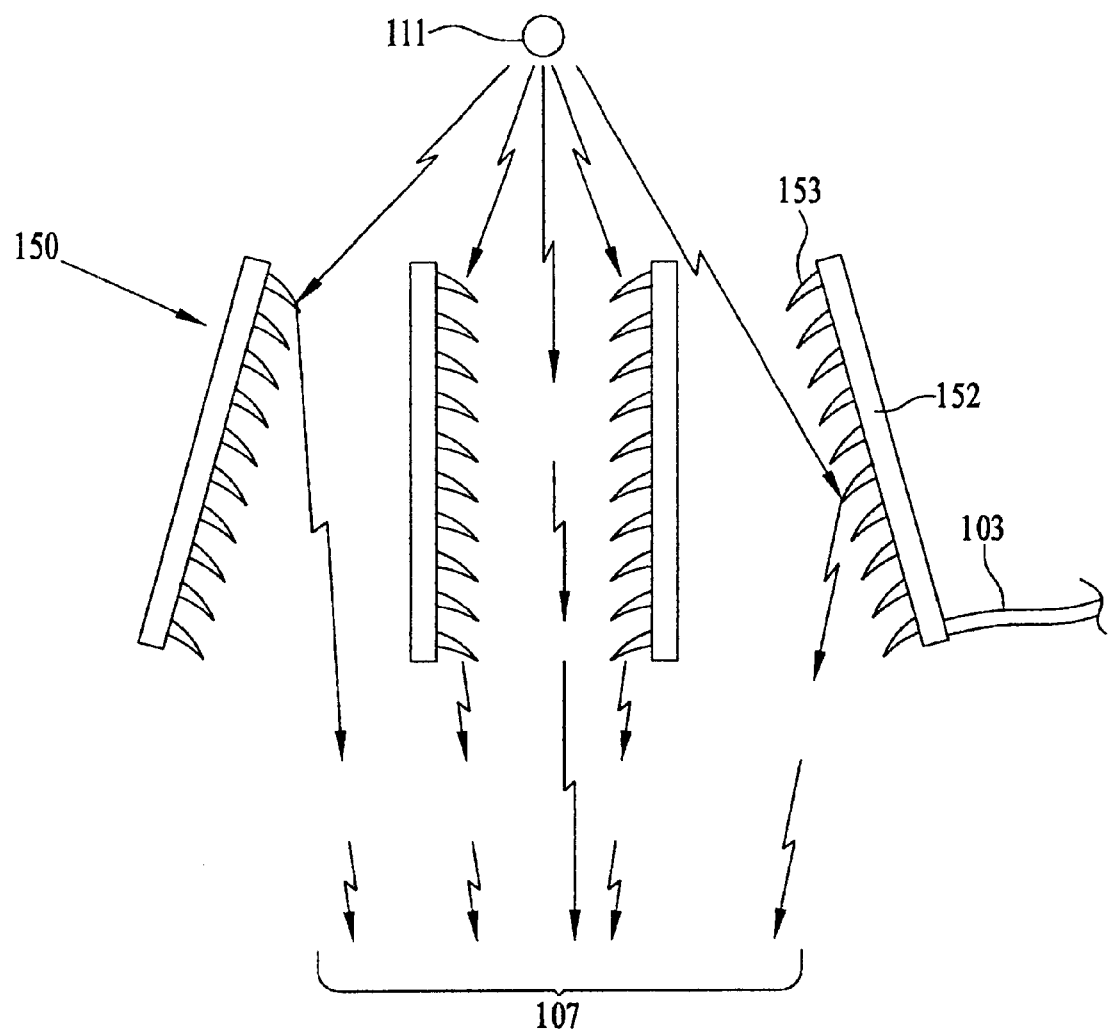
FIGS. 5b(i)–(ii) illustrate nested refractive lenses.

An alternative design is to use the dual lens or nested lens configurations of FIG. 5a(i), FIG. 5a(ii), FIG. 5b(i), and FIG. 5b(ii) to produce multiple focused beams, but each beam is directed to a corresponding detector module. In this instance multiple slit-like beams are shown. A similar design has been described previously, but narrow bandwidth x-ray mirrors were described rather than refractive lenses. Nelson et al., U.S. Pat. No. 4,958,363, describes such a design. The practicality of utilizing specific x-ray optic devices is influenced by several factors including: the size and distribution of the radiation source, the energy spectrum of the radiation, physical size limitations of the detectors used in the detector array, the imaging format, which may be an internal radionuclide source or an external radiation source, and space requirements, and the cost and maintenance of the x-ray optic devices. If the narrow bandwidth filtering directional discrimination properties of a x-ray mirror are not needed or the operational energy range is better suited to refractive or capillary x-ray optics then these devices may be preferred.

Turning to FIG. 5a(i) and FIG. 5a(ii), perspective views of configurable dual x-ray refractive lenses 150 that incorporate refractive slats 153 are shown. This design is similar in principle to a dual mirror x-ray telescope. The lens includes a support 152 for the refractive slats 153. This lens increases the apparent aperture of a slit-like or slot-like detector. The focal length of the lens needs to be accounted for when determining where to locate the lens relative to the source and detector.

As illustrated in FIG. 5b(i) and FIG. 5b(ii), this configuration may be modified and extended by nesting pairs of x-ray refractive lenses 150. The nested pairs of configurable or fixed refractive lenses 150 may be mounted in an assembly 151 similar to the nested x-ray mirror telescopes that have been used in x-ray astronomy for a number of years. Practical nested lens will require refractive lenses with thin shells used as supporting structures. The efficiency of the nesting technique will improve if the refractive lenses 150 can be densely packed. Therefore, a relatively thin support structure 151 is preferred.

Figure 6:
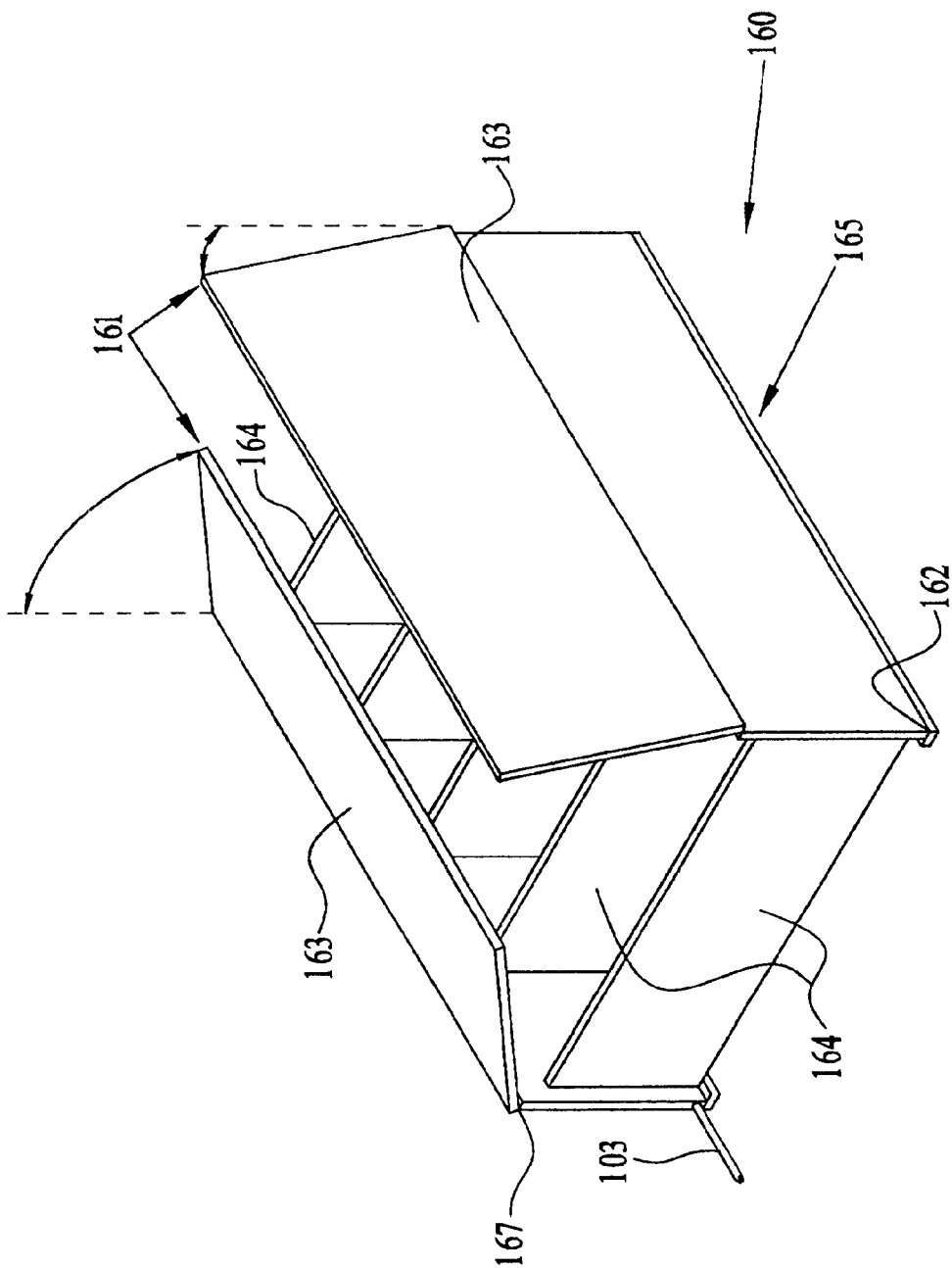
FIG. 6 illustrates a perspective view of an electronically controlled configurable collimator.

FIG. 6 shows a perspective view of an electronically-controlled configurable collimator 160 which uses electronically-controlled configurable elements, in this case two sets of configurable slats 161 or septa made from appropriate photon attenuating materials such as tin, lead, tungsten, or uranium. The two sets of adjustable slats 161 include a longer length slat set 163 and a set of shorter length slats 164. The collimator 160 includes hinges 162, 167 and a support frame 165 that facilitates the manipulation of the slats 161. The configurable collimator 160 can be implemented so that the slats 161 move independently or in synchrony, similar to the operation of window blinds. The long slats 163 running the length of the detector may replaced with slats that are subdivided such that each subdivided slat is individually manipulated for each corresponding detector element. The shorter slats 164 are configured so that a set of two shorter slats 164 defines the edges of a detector module 102, with one short slat 164 defining a distal edge and the other short slat 165 defining a proximal edge of the detector module 102. The slats 163, 164 may be manipulated through the use of devices such as actuators, miniature motors, and pulley mechanisms. Moreover, the collimator 160 is capable of being controlled remotely through its communications link 103. Collimator 160 may be utilized with the detector modules 102 of any of the detector arrays 1000 disclosed herein.

Configurable collimators may utilize actuators, including electromechanical biopolymers or piezo-drivers, small motors, micromachines, or screw drives, to control parameters such as aperture size and orientation. In alternative embodiments of the configurable collimator, refractive, diffractive, or reflective elements are substituted for the attenuating elements, thereby forming configurable x-ray optics. An immediate extension of this approach is to abut configurable collimators to create 2-D arrays of attenuating, reflective, diffractive, or refractive slats. For example, if reflective slats are made sufficiently small these elements will assume the role of micromirrors, resulting in highly-configurable micromirror array x-ray optics which can be electronically-controlled. Optical micromirrors are commercially available. Additional functionality can be added if each micromirror is constructed on an actuator or a deformable surface controlled by actuators. By manipulating the elevation as well as the tilt of the micromirrors, adaptive 3-D x-ray optics can be formed.

A variation of this device is to replace the x-ray mirror coatings with diffractive or refractive structures. In a similar manner, neutron mirror coatings or refractive or diffractive structures can be used with micromirrors for neutron radiography applications.

Configurable x-ray optics are useful not only for modifying the radiation incident on the radiation detector but also for modifying the radiation emitted by a radiation source, including a radionuclide or radiographic x-ray source. For example, the configurable dual x-ray refractive lenses 150 shown in FIG. 5a(i) and FIG. 5a(ii) use electro-active, electromechanical biopolymer actuators to adjust the refractive elements in the lenses.

Figures 7A, 7B, 7C:
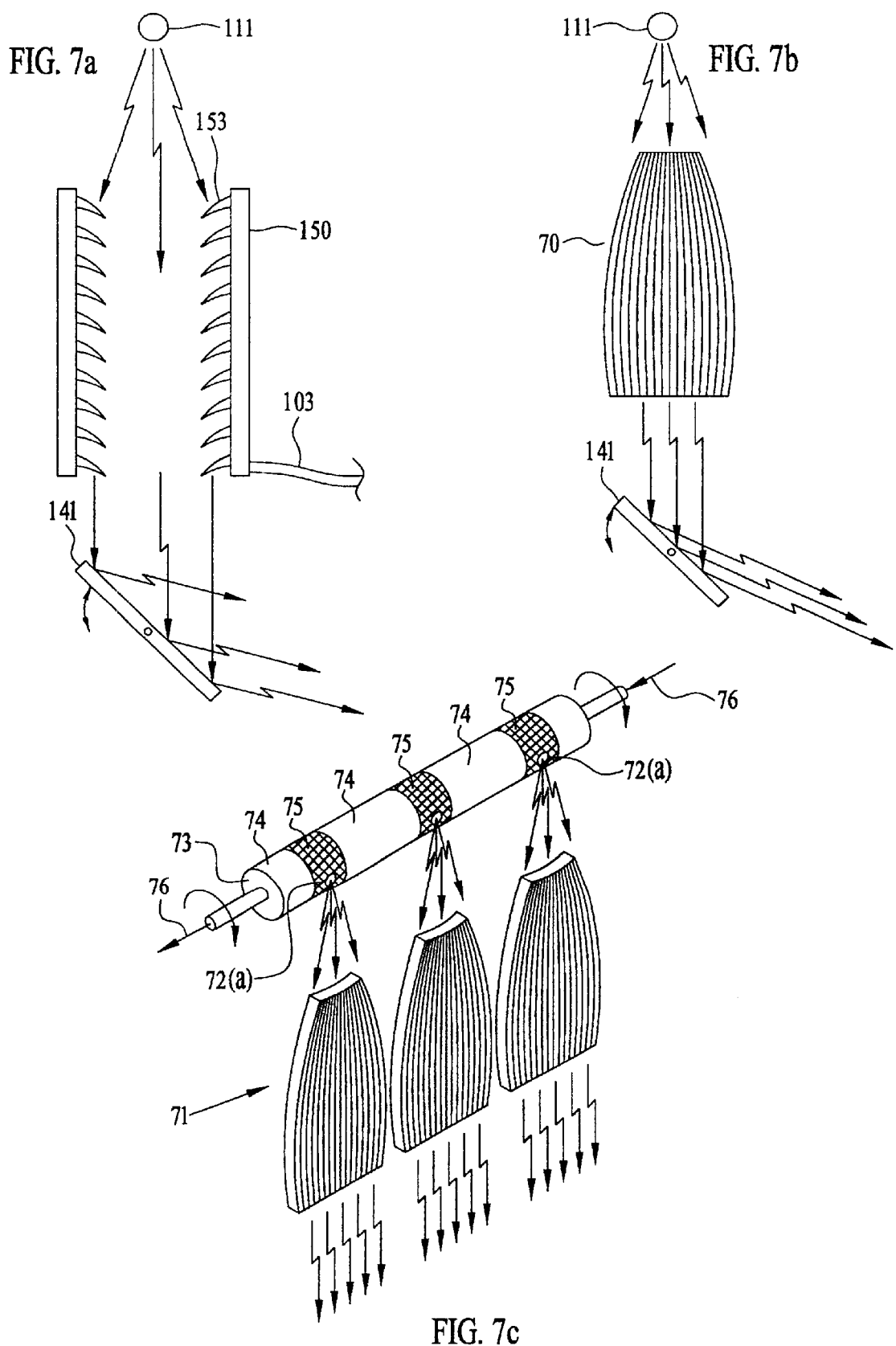
FIG. 7a illustrates an electronically controlled configurable refractive lens with an associated configurable x-ray mirror and radiation source.
FIG. 7b illustrates a fixed-focal length capillary x-ray lens with an associated configurable x-ray mirror and radiation source.
FIGS. 7c–7d illustrate an array of capillary x-ray optic lenses aligned with an array of radiation sources in the form of a cylindrical anode.

Turning to FIG. 7a, a perspective view of an electronically controlled configurable refractive lens 150 and a configurable, single element x-ray mirror 141 are illustrated. The apparatus in FIG. 7a provides an example of compound x-ray optics. The refractive slats 153 incorporate an electromechanical biopolymer material that functions as an electronically controlled actuator, thereby facilitating the manipulation of the refractive slats 153 without requiring a separate actuating mechanism. The tilt of each element can be electronically-controlled by manipulating the electro-active biopolymer material directly.

In FIG. 7b, the configurable refractive lens 150 is replaced with a fixed-focal length capillary x-ray lens 70, which is paired with the configurable, single element x-ray mirror 141. The x-ray mirror 141 provides spectral and directional filtering and is less expensive to manufacture than a focused x-ray mirror. If additional focusing is desired a focused x-ray mirror or a refractive x-ray lens could be used in place of the single element x-ray mirror 41. If additional spectral or directional filtering is not needed, then the flat x-ray mirror 141 can be eliminated.

The simple configurable collimator implementations describe herein preferably use electronically-controlled mechanical means to tilt rigid elements or flex elements into the desired position according to predetermined settings or based on detector feedback. More complicated implementations preferably use actuators or micromachines to adjust the surfaces of reflective or refractive elements. The technique of using detector feedback to control actuators is well-known in the field of adaptive optics where non-ionizing electromagnetic radiation is typically employed.

Figure 7D:
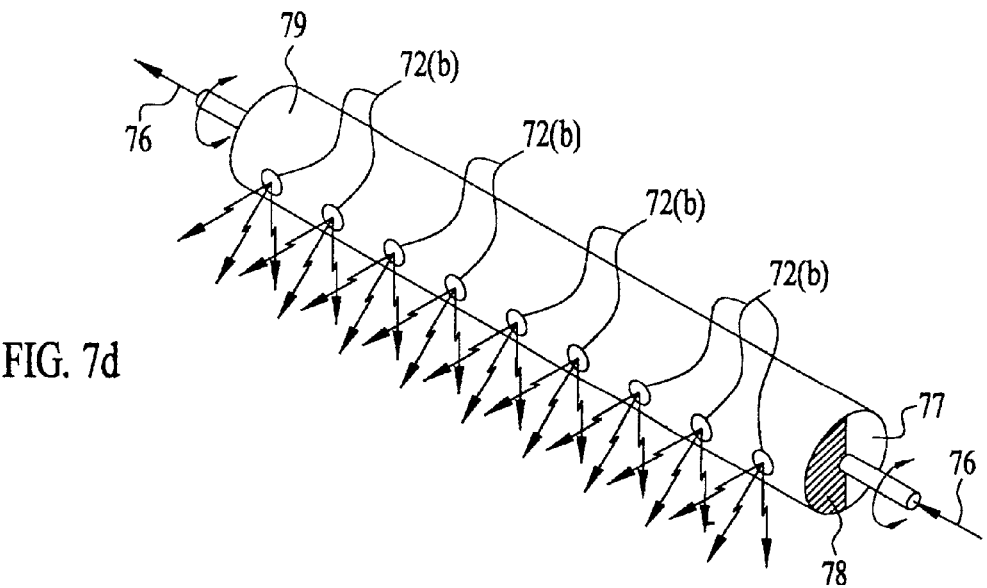
Figure 7E:
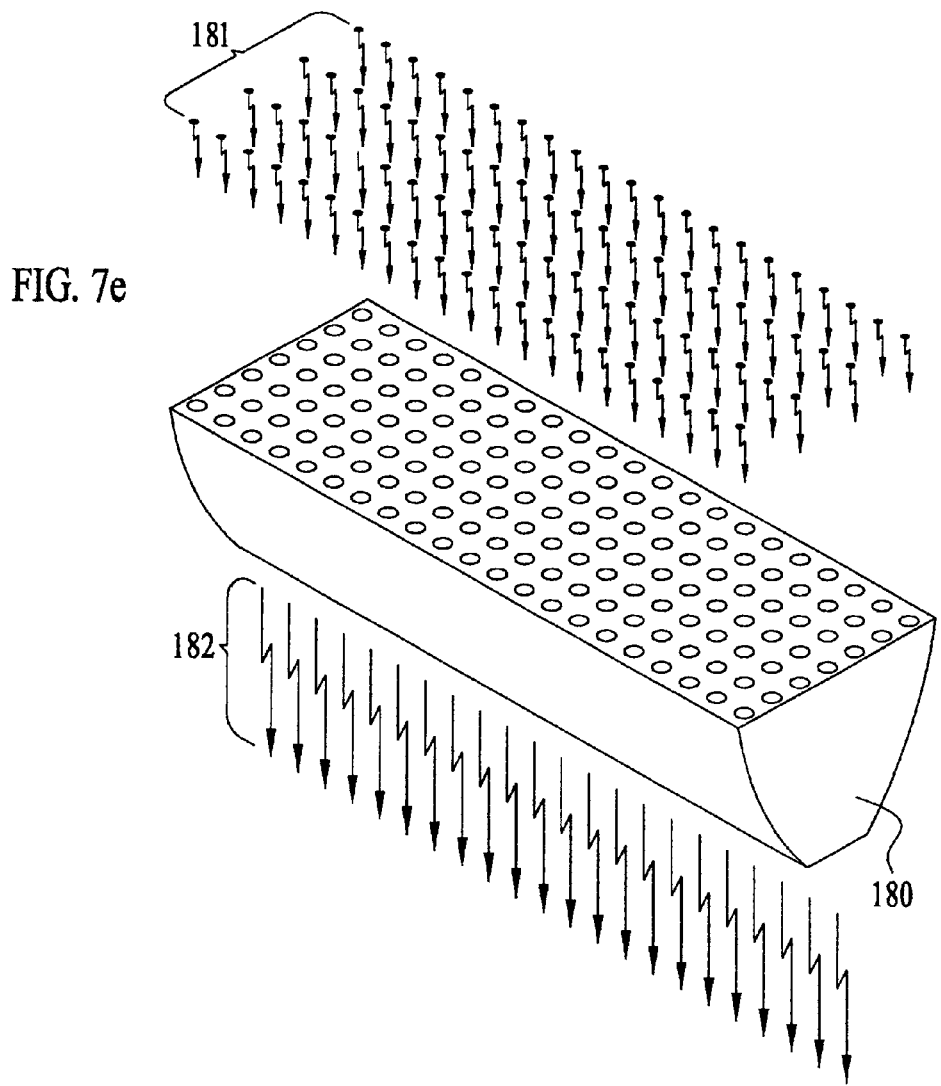
FIG. 7e illustrates a wedge-shaped capillary x-ray optic lens aligned with a dense array of radiation sources.

Turning now to FIG. 7e, another collimator encompassed by the present invention is illustrated. A wedge-shaped capillary x-ray optic lens 180 is aligned with a very dense array of radiation sources 181. The dense array of radiation sources 181 effectively forms a continuous source of radiation since the sources are packed in extremely close proximity to each other. This configuration allows the generation of a slit-like beam 182 from the radiation source 181. Here, the capillary x-ray lens 180 can be simplified for a slit scan application since focusing is only needed along one dimension. The wedge-shaped capillary lens 180 offers focusing along one direction, such as along the width of the slit. If adequate intensity can be obtained without focusing then a non-focusing capillary lens may be substituted into this configuration to function simply as a highly directional collimator. With this embodiment, a rotating cylindrical anode tube could also be used with the extended focal spot or the extended focal spot could be simulated using a fast scanning electron beam. Alternatively, other x-ray optic devices may be substituted for, or used in conjunction with, the capillary x-ray lens 180. This technique requires the use of x-ray optics of increased complexity further from the center of the focal spot due to the increasing angle of incident radiation at the x-ray optics, assuming the goal is to generate approximately parallel x-rays. An alternative to parallel scanning slits is to use slits in a radial geometry, permitting rotational scanning. This scanning format could be used in mammography with either flat or curved compression plates.

Another technique for reducing the scan time is to increase the number of scanning slits. The X-ray optics described in FIG. 5b(ii) could be employed for this purpose. As seen in FIG. 5b(ii), all slits and their detectors can share a single focal spot.

Alternatively, each slit can be aligned with its own focal spot. For example, a slit scanning system for mammography could use at least two x-ray tubes, i.e., two focal spots, each with a focusing x-ray optic collimator 70 and an aligned detector array 1000 on the other side of the subject, as seen in FIG. 9b.

Figure 8:
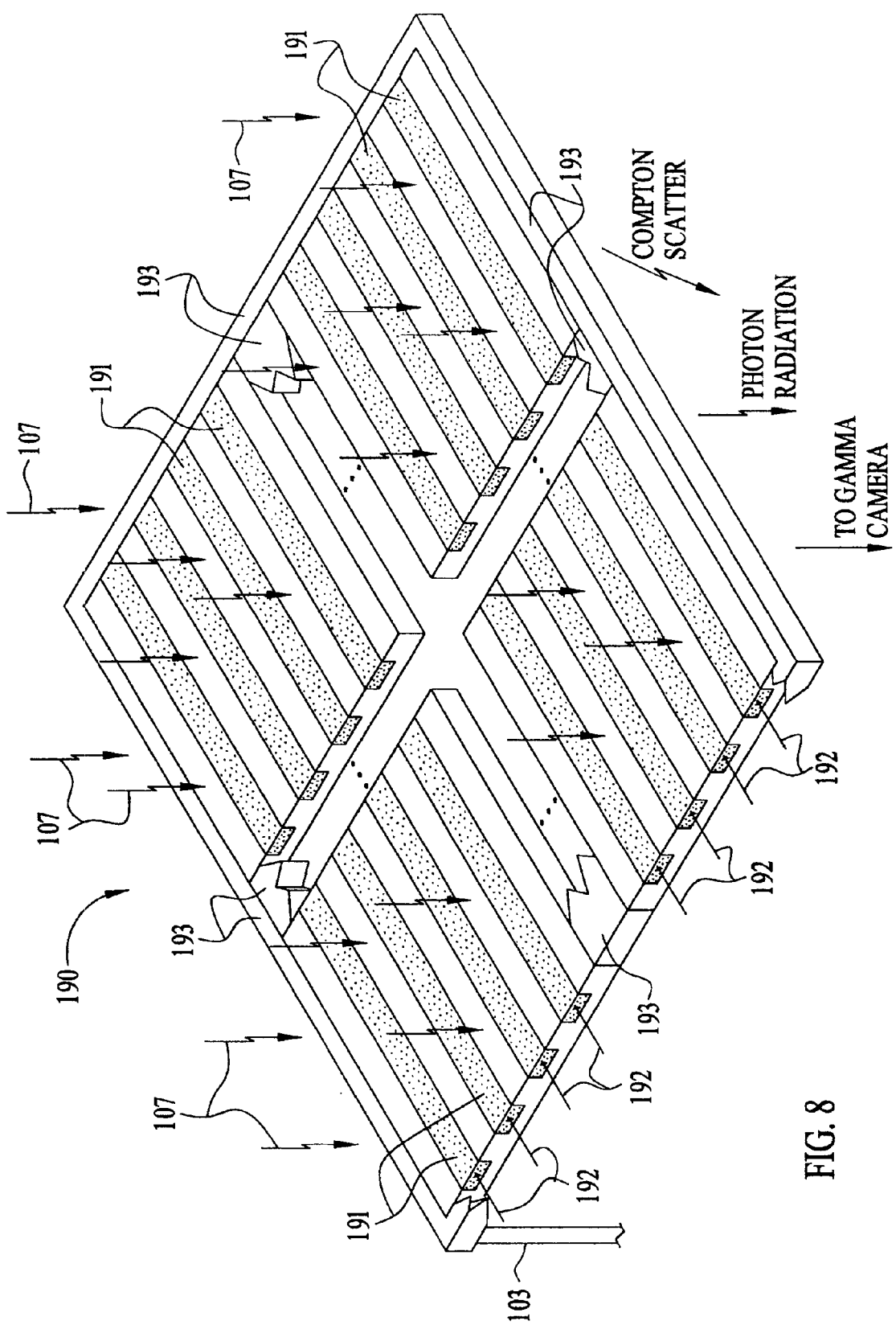
FIG. 8 illustrates a planar detector array comprised of strip detector modules positioned within a frame.

FIG. 8 illustrates a novel, unconventional collimator 190 that extends the principle of a detector array based on modules to a semiconductor Compton scatter detector array based on modules. This new collimator 190 preferably is used for nuclear medicine Compton scatter imaging. The new collimator 190 is also capable of being used with a standard Gamma camera or an array of detector modules to enhance the current Compton electronic Gamma camera design. FIG. 8 shows a perspective view of the Compton scatter module collimator 190 which preferably is a planar detector array comprised of strip detector modules 191, which are double-sided, crossed strips for 2-D resolution, positioned within a frame. In this implementation, modules 191 which incorporate relatively thin, linear or 2-D semiconductor detectors can be configured into a number of geometries compatible with the standard Gamma camera or array of detector modules. Relatively thin, linear or 2-D semiconductor detectors will be much less costly to manufacture than the thick, moderately large, 2-D semiconductor array detectors currently being tested and are therefore preferred.

The strip detector modules 191 shown in FIG. 8 are double-sided. The back-side strips (not shown) are oriented at 190 degrees to the front-side strips, thereby providing 2-D information. Compton scatter photon radiation is formed from this configuration and the radiation is detected by a Gamma camera. The Gamma camera preferably is located behind the collimator 190 and is not shown in FIG. 8. A connection 192 preferably is provided to transmit output from each detector module 191 to signal processing electronics. Module parameters, such as, e.g., temperature, electronic readout, and power are electronically controlled via the connection 192. In one embodiment, the modules 191 are also capable of interfacing with other modules 191 in order to share resources such as power, cooling, and communications. Fixed or configurable collimator geometries of greater complexity can be implemented as needed. A supporting frame 193 preferably is provided in order to maintain the positioning of the detector modules 191.

In one embodiment, the detectors modules 191 are immersed in a low temperature coolant in order to prevent operating temperatures that are too high. In this embodiment, all of the modules 191 can be encapsulated together in a container that holds the coolant. The collimator 190 can also be dithered to compensate for dead spaces between detectors that are closely spaced.

Imaging Systems

The present invention may also be employed in x-ray radiographic imaging systems. Operational energy ranges and spatial resolution requirements will be different in many instances from those that are used in nuclear medicine. Two additional factors that impact the design of nuclear medicine and x-ray radiography imaging systems are the image acquisition time and the properties of the radiation source. A consequence of the short acquisition times required in x-ray radiography, which are fractions of a second to multiple seconds for 3-D imaging, is the need for an intense radiation source or a subject who is not heavily attenuating. Some nuclear medicine study scan times can exceed 15 minutes. Typically both nuclear and x-ray radiographic imaging modalities benefit from an increase in the apparent intensity activity of the source. Benefits include reduced acquisition times and/or improved statistics. The source distribution and location are poorly defined in many nuclear medicine imaging applications, limiting the value of customized focused photon optics for directing more of the source radiation to a detector. In contrast to this situation, the source distribution, which is highly localized, and position are usually well-defined in x-ray radiography. Focusing x-ray optic collimators can be designed for a specific x-ray tube focal spot distribution. This would not be practical given cost constraints for most nuclear medicine imaging applications. X-ray radiography applications that could use one or more detector modules include slit, slot, or CT scanning.

X-ray mammography is a radiographic imaging application that uses relatively low x-ray energies, increasing the number of viable detector and unconventional collimator choices. For example, the source shown in FIG. 7b can be the focal spot of a x-ray tube. The tube is preferably a source with a well-defined location and reasonably well-defined directional and spectral properties. The focused capillary x-ray lens 70, or a refractive lens, a diffractive lens, a curved or configurable x-ray mirror, nested lens, or combinations of x-ray optic collimators, would be used to increase the intensity of radiation that would ultimately be detected by a slit-shaped detector, such as an edge-on detector, after passing through the subject. This configuration is illustrated in FIG. 9a.

Gantry Imaging Systems

Figure 9A:
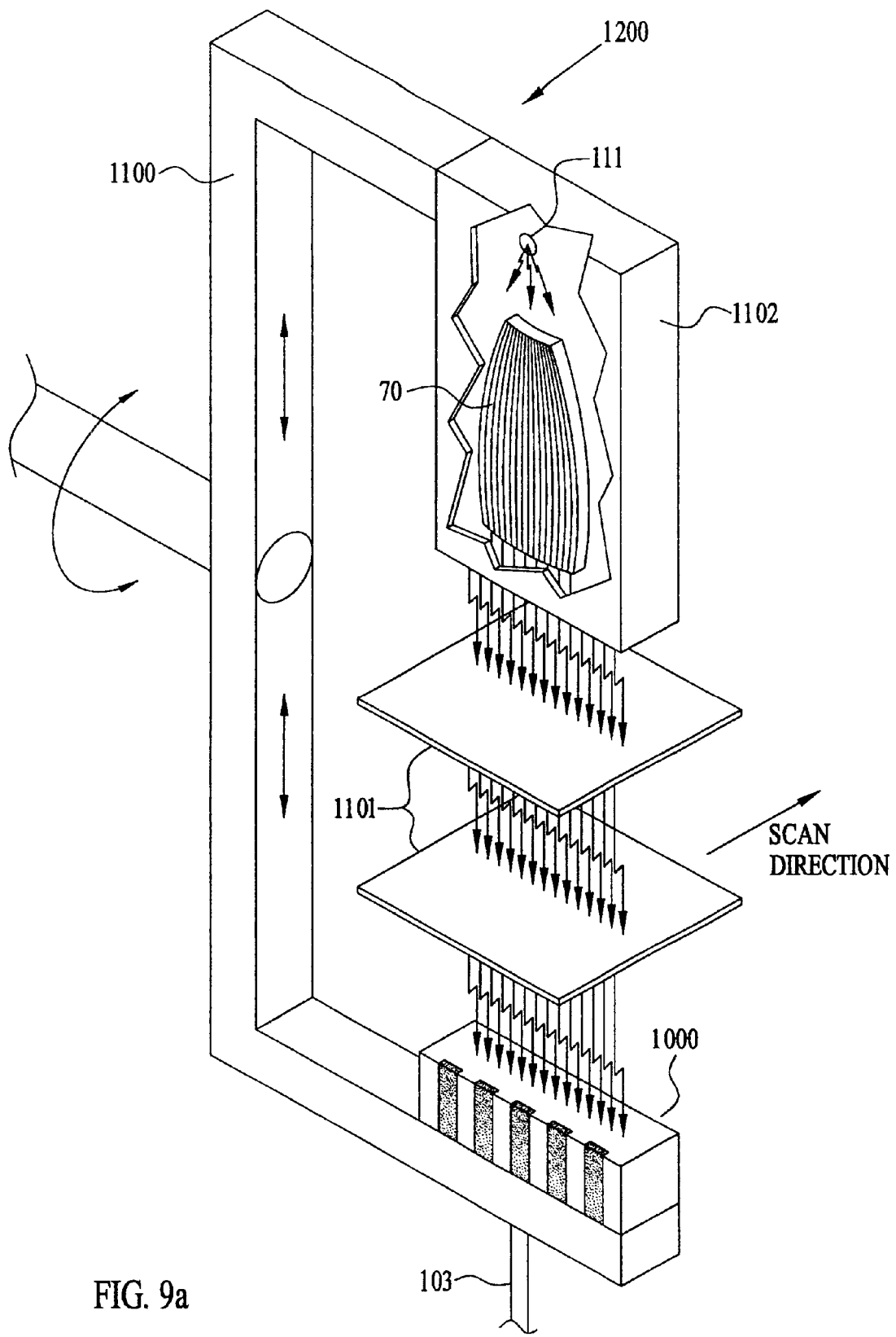
FIG. 9a illustrates a capillary x-ray lens system designed with a single gantry arm.
Figure 9B:
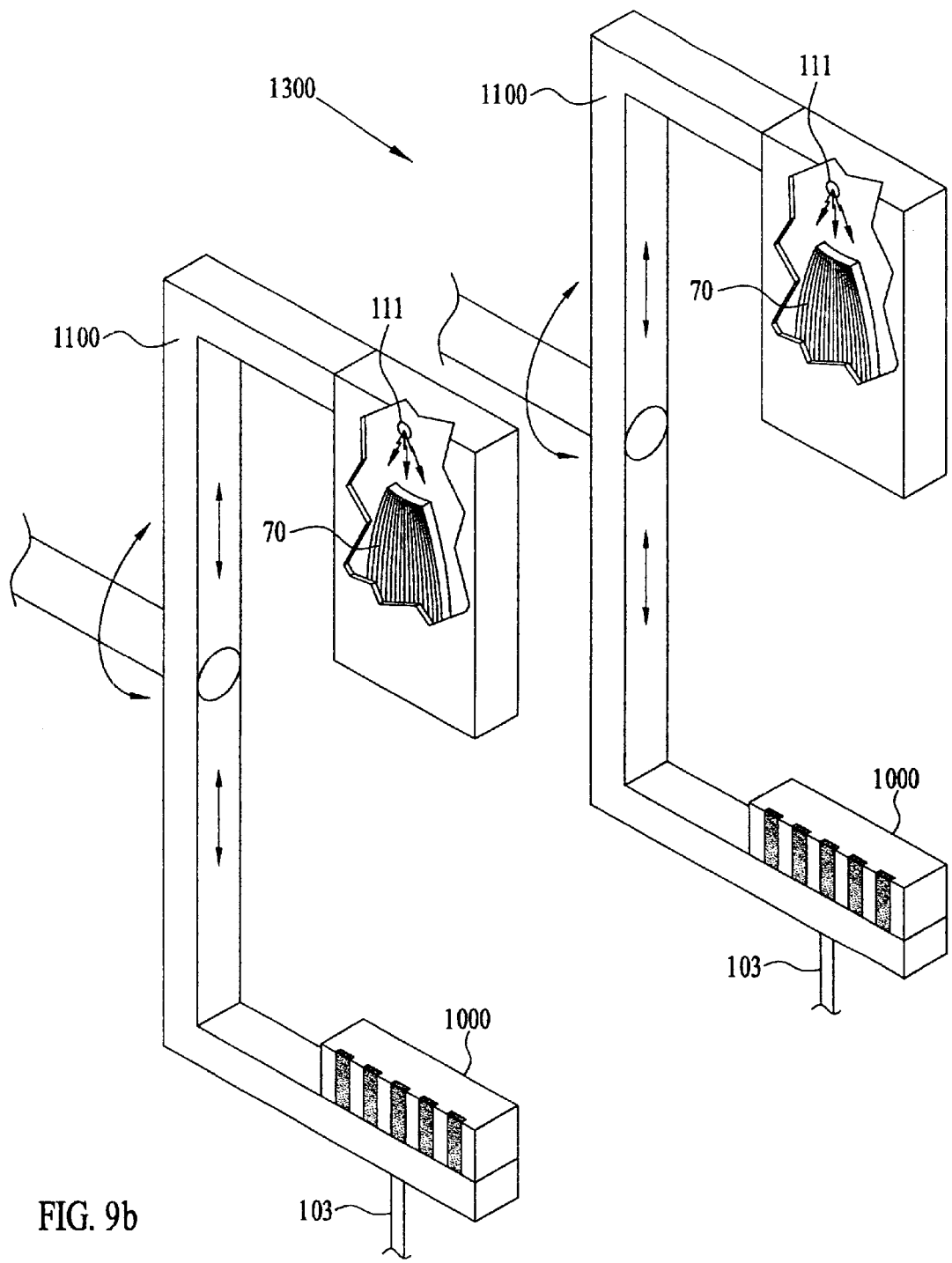
FIG. 9b illustrates a multiple gantry arm system.

Turning to FIG. 9a, a perspective view of a rotatable gantry unit 1200 with an adjustable arm 1100 configured to hold an x-ray tube 1102, incorporating a radiation source 111 and a capillary x-ray lens 70, and a detector array 1000 is shown. The array 1000 may use either analog or digital detector modules. The gantry system 1200 rotates about an axis and has an arm 1100 that allows for further adjustment in a bidirectional manner. As shown, the gantry system 1200 is adapted for x-ray mammography applications by incorporating a pair of compression plates 1101 that are used to position a subject breast. This design is comparable to a traditional x-ray film-screen mammography-imaging unit which utilizes a rotatable gantry. The x-ray tube 1102 is aligned with the detector array 1000. The x-ray tube 1102 and detector array 1000 are then scanned as a unit.

Figure 9C:
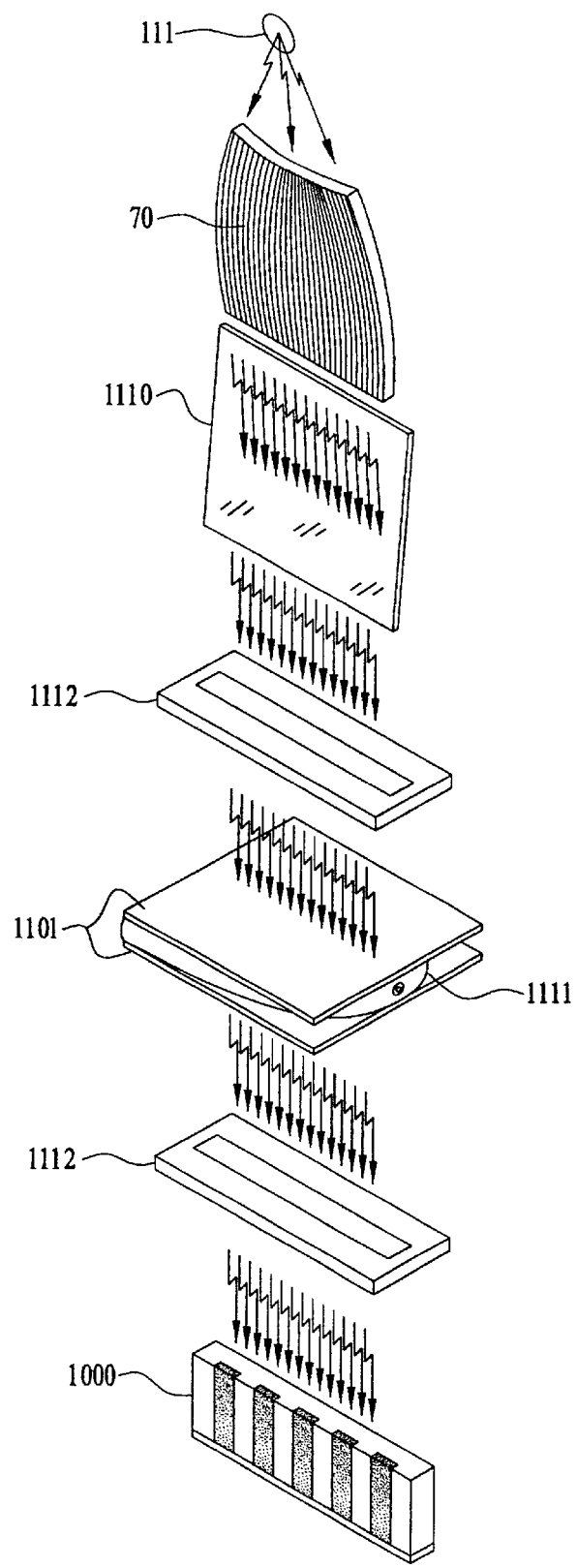
FIG. 9c illustrates a system utilizing additional x-ray optics introduced between a capillary x-ray lens and compression plates.

As seen in FIG. 9c, if additional spectral and directional filtering of the radiation beam is desired then a configurable x-ray mirror 1110 can be inserted between the capillary x-ray lens 70 and the compression plates 1101 holding the subject compressed breast 1111, as seen in FIG. 9c. A second x-ray mirror or crystal may be positioned between the compression plates 1101 and the detector array 1000 if even more spectral and directional filtering is desired. In some instances a refractive x-ray lens can be used in place of the x-ray mirror 1110, providing focusing and some filtering instead of the spectral and directional filtering provided by a configurable x-ray mirror. Collimators 1112 are provided on either side of the compression plates 1101 in order to limit the x-ray beams that are passed through the subject breast 1111. The collimators 1112 concentrate a segment of the x-ray source output into a slit or slot geometry.

Turning now to FIG. 9b, a dual gantry system 1300 that combines two individual gantry arms 1110 is illustrated. The separation distance between the gantry arms 1110 can be adjusted for scanning objects, for example, compressed breasts, of various sizes. As with the gantry system 1200 shown in FIG. 9a, the dual gantry system 1300 may also be rotated and the arms 1110 are adjustable in a bidirectional manner. Compression plates 1101 that are typically employed in mammography imaging may be incorporated into the dual gantry system 1300 but are not shown in FIG. 9b. An x-ray tube 1102, incorporating a radiation source 111 and a capillary x-ray lens 70, and a detector array 1000 are attached to each arm 1110 and are adjustable by virtue of being mounted on the arms 1100. Each unit would only be required to scan half as far as a single unit system, reducing the total scan time and x-ray tube operational time by 50%.

Many gantry designs are possible, including portable gantries designs, which are in use with portable x-ray and Gamma camera imaging systems. These gantry designs allow improved detector positioning with respect to the heart in comparison to standard Gamma camera designs.

Composite Anodes

The present invention is additionally directed to the generation of focused radiation by operating a composite anode operating in conjunction with x-ray optic lenses. Turning to FIG. 7c, a composite anode 73 comprised of N types of disks is illustrated. In this case N equals 2 and the disks preferably are molybdenum and rhodium, although N equals 1 or N greater than 2 can be constructed. For example, the disks are capable of being manufactured using other materials, such as, e.g., tungsten. Alternatively, another material may be added to the primary material used to manufacture the disk.

An array of capillary x-ray optic lenses 71 preferably is aligned with an array of radiation sources/focal spots 72(a) that project multiple electron beams incident to a rotating cylindrical anode to form an extended slit-like radiation beam generated by an extended radiation source. This configuration allows the radiation to be focused into the extended slit radiation beam. As discussed, the composite cylindrical anode 73 shown in FIG. 7c preferably is comprised of rhodium disks 74 and molybdenum disks 75. Shifting the tube laterally by one disk width while maintaining the positions of the focal spots 72 and capillary x-ray lens array 71 permits the selection of a specific anode spectrum. In the configuration shown in FIG. 7c, the choice is between a spectrum generated by the rhodium disks 74 and a spectrum generated by the molybdenum disks 75. Coolant 76 is passed through the anode 73 in order to facilitate the maintenance of an optimal operating temperature.

Other composite anode tube geometries are possible. For example, an anode could be built by combining 2 or more fractional, including half or quarter, circle cylinders. FIG. 7d illustrates an oscillating composite anode 79 comprised of two materials, each in the shape of a fractional circle cylinder. A plurality of focal spots 72(b) is located longitudinally on each fractional cylinder 77, 78. Two materials that are capable of being used to manufacture the fractional cylinders 77, 78 include rhodium and molybdenum. The configuration shown in FIG. 7d, as the configuration in FIG. 7c, allows for a choice of spectrums generated by the materials comprising the oscillating composite anode 79.

Another alternative geometry is evidenced in a continuous slit scan acquisition format. In a continuous slit scan acquisition format, the anode would oscillate through an arc slightly smaller than the fraction of a circle which the desired material, such as molybdenum, rhodium, or tungsten, occupies. In this case only a single material is used to determine the x-ray spectrum distribution.

Another alternative embodiment uses at least two full-sized anode cylinders comprised of different materials which can be shifted in and out of position so that the same electron beam source can be used. Only the anode that is being used to generate x-rays needs to rotate. This particular multiple-anode configuration is used so that the x-ray tube unit will remain reasonably compact.

Yet another alternative embodiment is to abut different and distinct anodes such that a single elongated anode is present. With this embodiment, an entire anode can be shifted depending on which anode material is desired.

This approach can be extended to the deployment of multiple focusing capillary x-ray lenses so that multiple slits or slots can be scanned at the same time using a single x-ray tube focal spot. A drawback to the use of a capillary lens to focus a small focal spot onto an extended slit is that the capillary x-ray optics will become more complex in order to direct radiation, in an approximately parallel direction, to sections of the slit which are far from the center of the slit. The capillary x-ray lens design can be simplified if the focal spot source or radiation source is reshaped to more closely match the shape of the slit or slot. The x-ray source can be modified such that additional focal spots are incorporated parallel to the length of the slit. An equal number of capillary x-ray lenses or a lens array with relaxed design constraints are abutted and aligned with the corresponding focal spots in the focal spot array of a rotating cylindrical anode x-ray tube.

Compression Plates

It should be noted that the use of compression plates to compress the area of the subject being imaged may be desirable. A reasonably small tissue path between the radiation source and the detector device is highly desirable in both nuclear medicine scintimammography and x-ray mammography. This reduces absorption, scatter, and in general improves image quality. In scintimammography partial, i.e., limited, breast compression can be used, allowing the detector device to move a few centimeters closer to a potential tumor. By comparison, more-strenuous compression is applied in standard x-ray mammography since the breast is under tension for a much shorter period of time. The sensitivity and specificity of scintimammography can be improved by using the information acquired in the initial scan to re-image suspicious regions. Re-imaging involves applying increased compression to a smaller section of the breast using contoured or flat compression plates of reduced area. Contoured and flat compression plates of reduced area, including versions with an open region in the compression plate, for optical imaging of tissue have been described by Nelson et al., U.S. Pat. No. 5,999,836, filed Feb. 2, 1996, which is fully incorporated herein by reference for all it discloses and describes. In a compression plate with an open region, the open region is located adjacent to the skin surface. This open region typically allows air and/or a coupling fluid/gel to be in contact with the skin surface. Radiation from an acoustic source can also be coupled into and out of the open region(s), enabling compression transmission and backscatter (reflection) acoustic image data and acousto-optic image data to be acquired as well as optical image data. The size and geometry of the open region in a compression plate can be customized according to the application.

A compression plate of reduced area refers to the actual plate surface which is used to compress a section of the breast to a uniform thickness relative to the surface of a typical compression plate which is used to compress the entire breast to a uniform thickness. For example, if a standard compression plate is translated with respect to the center of the breast such that approximately 50% of the breast are compressed uniformly, then this functions as a compression plate of reduced area. This additional level of compression permits a detector module array to be positioned nearer to a potential tumor. If a hole is included in the compression plate even closer positioning is possible while allowing other instruments, including instruments for ultrasound imaging, for optical imaging, and for injecting materials or obtaining tissue samples, to gain access to the compressed area. In some instances it is possible to forego the initial imaging of the entire breast and instead begin by imaging smaller sections, which are compressed with increased force relative to compression of the entire breast, if the total image acquisition time is acceptable. In this image acquisition format adjacent images should have sufficient overlap so that potential structures of interest will be visible in at least one image section.

The concept of compressing a smaller section of the breast more strenuously than would be tolerated for whole-breast compression in scintimammography in order to achieve greater local compression can be applied to x-ray mammography. One rather limited approach is to position the patient such that the left edge or right edge of a standard compression plate, approximately 24–30 cm×18–24 cm, is near the center line on the breast, slightly more than one-half of the breast could be compressed and scanned. A x-ray technologist would then reposition a compression plate relative to the breast such that the other half is compressed and scanned. If higher levels of compression are desired then one or both flat compression plates need to be reduced in size.

Contoured or flat compression plates, including plates with holes, that can compress only a section of a breast rather than the entire breast, as is practiced in x-ray film-screen mammography, may eliminate the need or simplify the requirements for items such as x-ray optics, multiple or extended focal spot sources, and multiple slits. X-ray tube power handling requirements could be reduced since continuous scanning occurs across a smaller area in comparison to conventional x-ray mammography imaging even if the compressed tissue thickness were to remain the same. Additionally, greater levels of compression can be attained if one or both of the plates of reduced size are contoured.

Figure 10A:
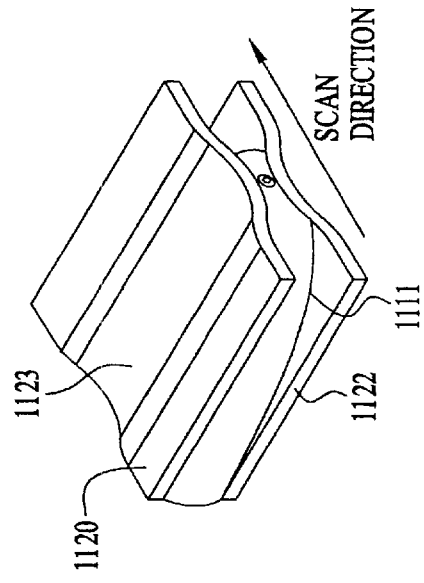
FIGS. 10a–10b illustrate a system incorporating flat and contoured compression plates.

Turning to FIG. 10a, a perspective view of a contoured upper compression plate 1120 that is appropriate for compressing a section of a breast 1111 is shown with the image scan area 1123 indicated. In this embodiment, the bottom compression plate 1121 is flat, simplifying the positioning of the breast 1111.

Figure 10B:
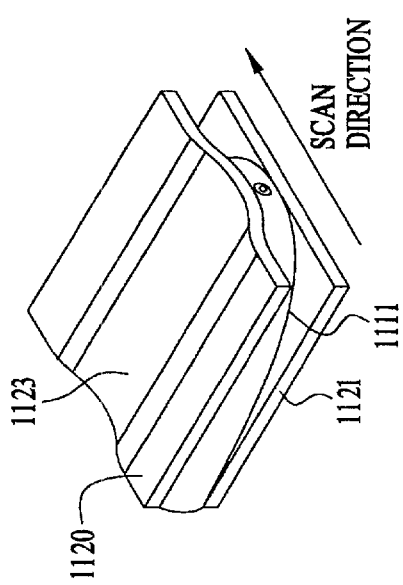

In FIG. 10b, the flat bottom compression plate is replaced by a second contoured compression plate 1122. This configuration enables additional compression of the breast 1111 as compared with the configuration illustrated in FIG. 10a.

Figure 10C:
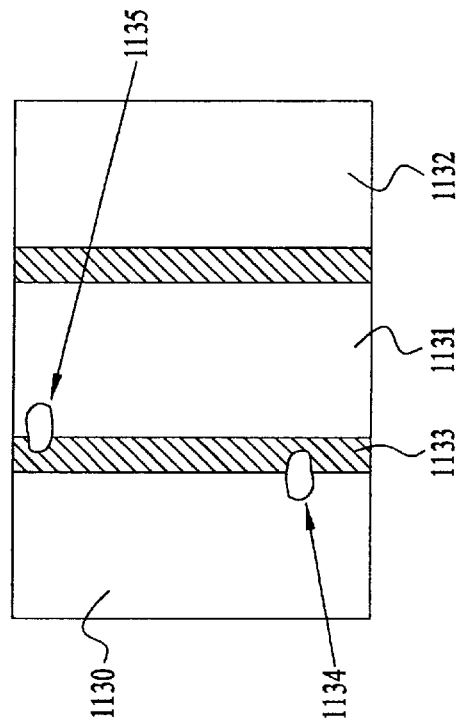
FIG. 10c illustrates the use of overlapping images to ensure complete imaging of the breast.

The present invention is also directed to a method of acquiring a series of overlapping successive sections or sub-images in order to increase image resolution of the subject. Turning to FIG. 10c, the overlap 1133 that is produced by acquiring successive image sections 1130, 1131, 1132 of the subject are illustrated. This overlap 1133 can be utilized to produce a continuous, higher resolution image. The overlap 1133 must be sufficient so that small structures 1134, 1135 may be viewed in at least a single image area. To acquire the successive image sections 1130, 1131, 1132, after each section is scanned, the compression plate or plates are repositioned relative to the breast before the next section is scanned. Efficient repositioning involves marking temporary spots on the breast or using a focused light beam on the breast in order to define the locations of the sections to be compressed. The compression plate or plates are repositioned such that a small overlap between adjacent sections occurs. This is continued until the entire breast is scanned. A series of high resolution breast section images can then be evaluated by a radiologist.

Section areas should be sufficiently large such that any structures of interest can be clearly discerned within at least one section image. Advantages include lower patient dose and higher spatial and contrast resolution, less stress on the x-ray source, reduced scatter, and the option to use a less-energetic x-ray spectrum. Additionally, if the procedure is video recorded, the image sections can be referenced to a video recording of the various positions of the compression plates in order to increase the accuracy of the scans. An alternative implementation of this technique is to acquire a complete scan initially and then selectively re-image problematic sections using increased compression.

Dynamic Acquisition of Images

The present invention is also directed to a process for dynamically acquiring partial images of a subject image in order to obtain an entire, optimized image of the subject. This method is particularly advantageous when utilized to acquire images of a breast. The process of image optimization based on the energy spectrum and integrated intensity while limiting patient risk is complicated by the fact that breasts are typically non-uniform in tissue composition and the tissue distributions are non-uniform. In order to determine a reasonable compromise x-ray spectrum it would be desirable to implement a static or dynamic pre-scan since both techniques permit dynamic acquisition of the mammography image. Image optimization is obtained by scanning a tissue volume that is no finer than the area of the slit or slot. A static pre-scan acquires an entire image at a low radiation level in order to determine the degree of attenuation while avoiding the radiation levels needed to acquire an acceptable image. After the pre-scan, the actual image is acquired based on all of the pre-scan data. In this case the tube voltage and current could be dynamically controlled during image acquisition. If the tube uses an array of radiation sources (see FIG. 7e) then individual sources or sub-arrays of sources can be configured as needed in order to provide the desired beam characteristics during a scan. A dynamic pre-scan uses two slits or slots which move in parallel. The first slit or slot is used to acquire the low radiation level data which is then used to dynamically and adaptively adjust the x-ray tube current and/or KV so that an acceptable signal-to-noise ration (SNR) is maintained for each tissue segment imaged by the second slit or slot.

Alternatively, the pre-scan may be avoided by adjusting the intensity, i.e., the current, and/or tube voltage dynamically ("on-the-fly") in order to maintain an acceptable SNR. A feedback system manipulates beam current and/or KV. At each slit or slot position, the current level is initially reduced and the detected output is analyzed. The beam current and/or tube KV is then increased to the appropriate level or the time the slit takes to scan a slit/slot area is increased so as to acquire adequate statistics. Alternatively, both the beam current and the scan time may be increased in order to acquire statistics. Another, less-complex, dynamic acquisition technique is to operate with a constant beam current and then track the time needed to acquire adequate statistics for each slit or slot area.

Single-slit and multi-slit designs are known to those skilled in the art of x-ray radiography. The utility of such designs can be enhanced by incorporating x-ray optics with traditional or novel focal spot configurations in conjunction with efficient detector modules. Additional benefits are gained in x-ray mammography and scintimammography by modifying the scanning procedure so that increased compression is implemented. Preferably, compression plates such as those described above and in FIG. 10a and FIG. 10b are utilized to implement the increased compression.

Correction and Tuning of an Array

The present invention is also directed to a novel method of correcting and tuning a detector array that preferably involves tracking one or a limited number of spheres, such as microspheres, or small capsules, said spheres or capsules containing known levels of radioactivity, as they are taken up by or circulate within the patient. These are collectively referred to as reference sources. Since the sizes, compositions, activities, and photon energies of the reference sources are known or are measured prior to their introduction into the patient, the scattering and absorption effects of tissue positioned between these reference sources and the detector can be measured directly once the reference sources are at the desired locations. The reference sources can be designed to be biodegradable or inert depending on how long or where they are expected to be within the body. The reference sources can have internal structures and non-uniform activity distributions. Typically the reference sources are introduced into the patient prior to the nuclear medicine test. The reference sources can also function as distinct, internal, small sources that can be measured with little or no interference from other reference sources. Individual reference sources can have distinctive properties such as different levels of radioactivity, different types of radionuclides, or the incorporation of magnetic, acoustic, inductive, or x-ray attenuating materials. These properties can be useful for identifying specific reference sources within the body, measuring the effects of tissue at different energies, helping to guide the reference source to a desired location, and providing position information by causing the reference source to absorb, reflect, or emit acoustic, EM, or ionizing radiation when interrogated by an external field. The reference sources can also be tracked as they move within the body. Once the relatively small reference sources are in the appropriate locations they also can be used to fine tune and focus the detector array for that specific imaging task. Thus, the position-dependent imaging capabilities of the detector array can be estimated for a patient. If the reference sources are sufficiently distinct from the radionuclides introduced into the patient during a nuclear medicine test then estimating attenuation and focusing can be done dynamically, permitting adaptive imaging.

The concept of adaptive imaging is utilized in many imaging applications. In particular, the use of artificial guide-stars is well-known in Astronomy. An important difference between our reference source and a guide-star is that the intensity of the guide-star is not particularly important. The guide-star is used to correct phase distortions to an optical wavefront due to a turbulent atmosphere. The method of the present invention attempts to estimate attenuation corrections and use the reference source to help focus the detector array at approximately the position of the actual radionuclide distribution. The correction and tuning/focusing method along with appropriate reference sources can also used with existing Gamma cameras, PET scanners, etc.

The present invention is additionally directed to a process of calibrating a detector module array using a known source distribution. Electronic calibration of a detector module array involves using a known source distribution such that the responses of individual detector modules can be balanced either electronically or through software amplification of the digitized data. This calibration effort will include evaluating detection events that are recorded by more than one detector module, which is similar to the Gamma camera problem of evaluating detection events recorded by multiple PMTs. Typical source distributions include collimated spots, slits, slots, or flat fields with appropriate energy distributions. It is assumed that source energy distribution is appropriate for the imaging task the detector modules will be used for. If the detector offers energy resolution then an additional calibration can be performed to account for energy resolution. The energy-dependent Modulation Transfer Function (MTF (E)) can be measured over the expected energy range of the x-ray source or from a series of measurements involving narrow band sources with different energies.

The process may be applied to the radiographic imaging application of x-ray mammography. The x-ray source properties are well-defined. In traditional x-ray film-screen mammography using an integrating detector, the intensity of the x-ray field decreases or falls off as the position changes from the center to the edge of the x-ray field. The result is a divergent beam from the focal spot, said focal spot being a point-like x-ray source. Calibration of this relatively large, planar, x-ray field is typically not done. Next consider replacing the film-screen detector with a detector array comprised of a single detector module which is appropriate for slit-scan imaging. Once the detector module is aligned with respect to the x-ray source then a calibration can be performed that approximately corrects for the variations of the x-ray beam intensity at the locations of the detector module detector pixels. This results in a position-dependent, energy-dependent, intensity profile. For example, if the slit-like detector module uses an edge-on detector, the intensity of the slit-like x-ray beam along the length of the detector can be measured. The spectral distribution of a typical Mo-anode or W-anode mammography x-ray tube is relatively broad band, usually greater than 10 KeV. This implies that the information content of detected photons at the upper and lower extremes of the spectral band can be substantially different for the typical x-ray energies used in film-screen mammography. If the edge-on detector is capable of providing sufficient energy resolution, such as when an energy-resolving detector rather than an integrating detector is utilized, then additional information is available. Each detected photon represents the exponential attenuation properties of the filter, which in the case of mammography is breast tissue. The filter, due to its attenuation properties, modifies the local x-ray beam intensity and spectral distribution at each detector pixel. If the spectral distribution is uniform along the length of the detector then a reasonable comparison of corrected intensity and spectral content between individual pixels in the detected image can be made. What is essentially acquired is a set of overlapping energy-dependent images. If energy-dependent MTF (MTF (E)) measurements are available, then an improved analysis of the energy-dependent images is possible. If the spectral distribution of the source is not uniform along the length of the detector then the position-dependent, source spectral intensity distribution can be measured and used to approximately correct the detected data.

An alternative embodiment of this process involves narrowing the x-ray beam bandwidth about an appropriate energy for a particular breast type, adjusting for size and composition. This modification simplifies the detection and analysis process for both integrating detectors and energy-resolving detectors. Configurations of detectors that would be appropriate for use in this embodiment of the process are described above and in FIG. 5a(i)–(ii), FIG. 5b(i)–(ii) and FIGS. 7a–7d.

It is desirable to measure the detector MTF (E) at the appropriate energy. In addition, a narrow bandwidth filter may be utilized in order to reduce patient risk by removing radiation energies which are totally absorbed by the breast or represent relatively little information about the properties of breast tissue.

Although the embodiments of the present invention have been described in terms of its use for nuclear medicine and x-ray mammography applications, the present invention may also be used for other medical radiographic imaging applications as well as industrial and scientific applications. For example, similar designs can be used with appropriate radiation collimators such as neutron mirrors or electron optics for imaging sources of neutrons or charged particles, respectively. Radiological and non-medical applications which utilize composition analysis based on Compton scatter measurements and/or tomographic imaging will also benefit from this design. Unconventional collimators such as x-ray optic, configurable, and Compton scatter collimators can be used with standard Gamma cameras to improve the capabilities of these devices.

While the invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

What is claimed is:

1. An electronically configurable collimator system, use in gamma and X-ray imaging devices comprising:

a first set of adjustable slats, a second set of adjustable slats, wherein the tilt angle of the first set of slats and the tilt angle of the second set of slats are individually adjustable by electronic means, and a support frame designed to secure the first and second set of adjustable slats, wherein the first set of adjustable slats is positioned along the support frame in an orientation corresponding to a long edge of a detector module, and the second set of adjustable slats is positioned along the support frame in an orientation corresponding to a short edge of a detector module.

2. The collimator system of claim 1 wherein the first and second sets of slats are capable of adjustment independently of each other.

3. The collimator system of claim 1 wherein the first set of adjustable slats is divided into subdivisions, each subdivision corresponding to a detector, and wherein each subdivision is capable of being manipulated independently of other subdivisions.

4. The collimator system of claim 1 wherein the second set of adjustable slats is divided into subdivisions, each subdivision corresponding to a detector, and wherein each subdivision is capable of being manipulated independently of other subdivisions.

5. The collimator system of claim 1 wherein the first and second sets of adjustable slates are both subdivided such that each subdivision is capable of being manipulated independently of other subdivisions.

6. The collimator system of claim 1 further comprising:

a manipulation subsystem capable of adjusting the adjustable slats comprising manipulation devices taken from the group consisting of actuators, miniature motors, pulley mechanisms, electro-mechanical biopolymer actuators, piezo-drivers, micromachines, and screw drives.

7. The collimator system of claim 1 wherein the first and second set of adjustable slats are made of material chosen from the group consisting of photon attenuating material, reflective material, diffractive material, and refractive material.

* * * * *